(12) United States Patent
Smithyman et al.

(10) Patent No.: US 10,386,326 B2
(45) Date of Patent: Aug. 20, 2019

(54) FLEXIBLE ELECTRICAL DEVICES AND METHODS

(71) Applicant: Florida State University Research Foundation, Inc., Tallahassee, FL (US)

(72) Inventors: Jesse Smithyman, Oakland, CA (US); Zhiyong Liang, Tallahassee, FL (US)

(73) Assignee: The Florida State University Research Foundation, Inc., Tallahassee, FL (US)

(*) Notice: Subject to any disclaimer, the term of this patent is extended or adjusted under 35 U.S.C. 154(b) by 239 days.

(21) Appl. No.: 15/281,257

(22) Filed: Sep. 30, 2016

(65) Prior Publication Data

US 2017/0016848 A1    Jan. 19, 2017

Related U.S. Application Data

(62) Division of application No. 14/471,750, filed on Aug. 28, 2014, now Pat. No. 9,478,363.

(Continued)

(51) Int. Cl.
*G01N 27/404* (2006.01)
*B82Y 30/00* (2011.01)
(Continued)

(52) U.S. Cl.
CPC .......... *G01N 27/4075* (2013.01); *B82Y 30/00* (2013.01); *G01N 27/223* (2013.01); *G01N 27/308* (2013.01); *H01G 4/30* (2013.01); *H01G 9/00* (2013.01); *H01G 11/08* (2013.01); *H01G 11/26* (2013.01); *H01G 11/36* (2013.01); *H01G 11/54* (2013.01); *H01G 11/56* (2013.01); *H01G 11/82* (2013.01); *H01G 11/84* (2013.01);
(Continued)

(58) Field of Classification Search
None
See application file for complete search history.

(56) References Cited

U.S. PATENT DOCUMENTS 4,083,765 A    4/1978  Lawson
4,664,761 A    5/1987  Zupancic et al.
(Continued)

FOREIGN PATENT DOCUMENTS

JP    2006066187    3/2006

OTHER PUBLICATIONS

Choi, B.G. et al., "Facilitated Ion Transport in All-Solid-State Flexible Supercapacitors", ACS Nano, 5, 2011, pp. 7205-7213.
(Continued)

*Primary Examiner* — Susan D Leong
(74) *Attorney, Agent, or Firm* — Eversheds Sutherland (US) LLP

(57) ABSTRACT

Flexible electrical devices are provided that include a coated inner carbon nanotube electrode that has an exterior surface, an outer carbon nanotube electrode disposed on the exterior surface of the coated inner carbon nanotube electrode, and an overlap region in which the coated inner carbon nanotube electrode and the outer carbon nanotube electrode overlap one another, in which the device has a fiber-like geometry and first and second electrode ends. Methods are provided for fabricating an electrical component that includes a flexible electrical component having a fiber-like geometry and includes carbon nanotube electrodes.

12 Claims, 23 Drawing Sheets

Related U.S. Application Data

(60) Provisional application No. 61/870,859, filed on Aug. 28, 2013.

(51) Int. Cl.

| | | |
|---|---|---|
| *G01N 27/30* | (2006.01) | |
| *H01G 11/26* | (2013.01) | |
| *H01G 11/36* | (2013.01) | |
| *G01N 27/407* | (2006.01) | |
| *H01G 11/56* | (2013.01) | |
| *H01M 4/36* | (2006.01) | |
| *H01M 4/583* | (2010.01) | |
| *H01M 4/96* | (2006.01) | |
| *H01G 11/86* | (2013.01) | |
| *H01M 4/04* | (2006.01) | |
| *G01N 27/22* | (2006.01) | |
| *H01G 9/00* | (2006.01) | |
| *H01G 4/30* | (2006.01) | |
| *H01G 11/54* | (2013.01) | |
| *H01G 11/82* | (2013.01) | |
| *H01G 11/08* | (2013.01) | |
| *H01G 11/84* | (2013.01) | |
| *H01M 8/1018* | (2016.01) | |
| *H01M 4/02* | (2006.01) | |
| *H01M 4/66* | (2006.01) | |
| *H01M 10/05* | (2010.01) | |
| *H01M 10/058* | (2010.01) | |
| *H01M 10/38* | (2006.01) | |

(52) U.S. Cl.
CPC .......... *H01G 11/86* (2013.01); *H01M 4/0407* (2013.01); *H01M 4/366* (2013.01); *H01M 4/583* (2013.01); *H01M 4/96* (2013.01); *H01M 4/663* (2013.01); *H01M 10/05* (2013.01); *H01M 10/058* (2013.01); *H01M 10/38* (2013.01); *H01M 2004/022* (2013.01); *H01M 2008/1095* (2013.01); *H01M 2300/0082* (2013.01); *Y02E 60/13* (2013.01); *Y10T 29/417* (2015.01); *Y10T 29/49115* (2015.01)

(56) References Cited

U.S. PATENT DOCUMENTS

| | | | |
|---|---|---|---|
| 5,036,704 A | 8/1991 | Pusatchioglu et al. | |
| 6,709,471 B2 | 3/2004 | Miyamoto | |
| 7,553,341 B2* | 6/2009 | Pan .................. | H01G 11/36 257/E21.008 |
| 2012/0014038 A1* | 1/2012 | Meng ................ | H01G 11/26 361/502 |
| 2015/0147573 A1* | 5/2015 | Zhang ................ | B82Y 10/00 428/408 |

OTHER PUBLICATIONS

Jost, K. et al., "Carbon coated textiles for flexible energy storage", Energy Environ. Sci., 4, 2011, pp. 5060-5067.
Nyholm L. et al., "Toward Flexible Polymer and Paper-Based Energy Storage Devices", Advanced Materials, vol. 23, Issue 33, Sep. 1, 2011, pp. 3751-3769.
Chen, Z. et al., "Humidity Sensors: A Review of Materials and Mechanisms", Sensor Letters, vol. 3, No. 4, 2005, pp. 274-295.
Barisci, J.N. et al., "Electrochemical studies of single-wall carbon nanotubes in aqueous solutions", Journal of Electroanalytical Chemistry, vol. 488, Issue 2, Jul. 14, 2000, pp. 92-98.
Woo, Seung L. et al., "High-power lithium batteries from functionalized carbon-nanotube electrodes", Nature Nanotechnology 5, 2010, pp. 531-537.
Zhu, W. et al., "Durability Study on SWNT/Nanofiber Buckypaper Catalyst Support for PEMFCs", Journal of the Electrochemical Society, vol. 156, Issue 9, 2009, pp. B1099-B1105.
Fu, Y. et al., "Integrated power fiber for conversion and storage", Energy Environmental Science, 6, 2013, pp. 805-812.
Bae, J. et al., "Single-Fiber-Based Hybridization of Energy Converters and Storage Units Using Graphene as Electrodes", Advanced Materials, vol. 23, Issue 30, Aug. 9, 2011, pp. 3446-3449.
Kozlov, M.E. et al., "Spinning Solid and Hollow Polymer-Free Carbon Nanotube Fibers", Advanced Materials, vol. 17, Issue 5, 2005, pp. 614-617.
Shin, S.R. et al., "DNA-Wrapped Single-Walled Carbon Nanotube Hybrid Fibers for supercapacitors and Artificial Muscles", Advanced Materials, vol. 20, Issue 3, 2008, pp. 466-470.
Honda, Y. et al., "Effect of MWCNT Bundle Structure on Electric Double-Layer Capacitor Performance", Electrochemical and Solid-State Letters, vol. 12, Issue 3, 2009, pp. A45-A49.
Futaba, D.N. et al., "Shape-engineerable and highly densely packed single-walled carbon nanotubes and their application as supercapacitor electrodes", Nature Materials, 5, Nov. 26, 2006, pp. 987-994.
Shen, J. et al., "How carboxylic groups improve the performance of single-walled carbon nanotube electorchemical capacitors", Energy & Environmental Science, 4, 2011, pp. 4220-4229.
Jurewicz, K. et al., "Capacitance properties of multi-walled carbon nanotubes modified by activation and ammoxidation", Carbon, vol. 44, Issue 12, 2006, pp. 2368-2375.
Xu, B. et al., "Competitive effect of KOH activation on the electrochemical performances of carbon nanotubes of EDLC: Balance between porosity and conductivity", Electrochimica Acta, vol. 53, Issue 26, 2008, pp. 7730-7735.
Zhao, X. et al., "Spray deposition of steam treated and functionalized single-walled and multi-walled carbon nanotube films for supercapacitors", Nanotechnology, vol. 20, No. 6, 065605, 2009, 9 pages.
Chen, T et al., "Synthesis of aligned carbon nanotube composite fibers with high performances by electrochemical deposition", Journal of Materials Chemistry A, 1, 2013, pp. 2211-2216.
Wang, K. et al., "High-Performance Two-Ply Yarn Supercapacitors Based on Carbon Nanotubes and Polyaniline Nanowire Arrays", Advanced Materials, vol. 25, Issue 10, Mar. 13, 2013, pp. 1494-1498.
Cai, Z. et al. "Flexible, weavable and efficient microsupercapacitor wires based on polyaniline composite fibers incorporated with aligned carbon nanotubes", Journal of Materials Chemistry A, 1, 2013, pp. 258-261.
Meng, F. et al., "Carbon Nanotube fibers for electrochemical applications: effect of enhanced interfaces by an acid treatment", Nanoscale, 4, 2012, pp. 7464-7468.
Chen, X. et al., "Novel Electric Double-Layer Capacitor with a Coaxial Fiber Structure", Advanced Materials, vol. 25, Issue 44, Nov. 26, 2013, pp. 6436-6441.
Kaempgen, M. et al., "Printable Thin Film Supercapacitors Using Single-Walled Carbon Nanotubes", Nano Letters 9, 2009, pp. 1872-1876.
El-Kady, M.F. et al., "Laser Scribing of High-Performance and Flexible Graphene-Based Electrochemical Capacitors", Science, vol. 335, Mar. 16, 2012, pp. 1326-1330.
Zakhidov, A.A. et al., "Electrochemically Tuned Properties for Electrolyte-Free Carbon Nanotube Sheets", Advanced Functional Materials, vol. 19, Issue 14, Jul. 14, 2009, pp. 2266-2272.
Zhong, X.H. et al., "Continuous Multilayered Carbon Nanotube Yarns,"Advanced Materials, vol. 22, Issue 6, Feb. 9, 2010, pp. 692-696.
Foroughi, J. et al., "Preparation and characterization of hybrid conducting polymer-carbon nanotube yarn", Nanoscale 4, 2012, pp. 940-945.
Sun, G. et al., "Electrochemical Capacitive properties of CNT fibers spun from vertically aligned CNT arrays", Journal of Solid State Electrochemistry, vol. 16, Issue 5, 2012, pp. 1775-1780.
"Basic Research Needs for Electrical Energy Storage", Office of Basic Energy Sciences Department of Energy, Jul. 2007.

(56) References Cited

OTHER PUBLICATIONS

Mirfakhrai, J. et al., "Electrochemical actuation of carbon nanotube yarns", Smart Mater. Struct. 16, 2007, pp. S243-S249.
Mirfakhrai, T. et al., "Carbon Nanotube Yarn Actuators: An Electrochemical Impedance Model", Journal of Electrochemical Society, vol. 156, No. 6, Issue 6, 2009, pp. K97-K103.
Kimizuka, O. et al., "Electrochemical doping of pure single-walled carbon nanotubes used as supercapacitor electrodes", Carbon, vol. 46, Issue 14, 2008, pp. 1999-2001.
Rafailov, P.M., "Electrochemical functionalization of SWNT bundles in acid and salt media as observed by Raman and X-ray photoelectron spectroscopy", Physica Status Solidi (b), vol. 245, Issue 10, 2008, pp. 1967-1970.
Jang, J.H. et al., "Complex Capacitance Analysis of Porous Carbon Electrodes for Electric Double-Layer Capacitors", Journal of Electrochemical Society, vol. 151, Issue 4, 2004, pp. A571-A577.
Izadi-Najafabadi, A. et al., "Extracting the Full PoteAf Single-Walled Carbon Nanotubes as Durable Supercapacitor Electrodes Operable at 4 V with High Power and Energy Density", Advanced Materials, vol. 22, Issue 35, Sep. 15, 2010, pp. E235-E241.
Gogotsi, Y. et al., "True Performance Metrics in Electrochemical Energy Storage", Science 18, vol. 334, Nov. 18, 2011, pp. 917-918.
Shuk, P., "Solid-state humidity sensors", Solid State Ionics, 86-88, 1996, pp. 995-1000.
Jang, J.H. et al., "Complex Capacitance Analysis on Leakage Current Appearing in Electric Double-Layer Capacitor Carbon Electrode", Journal of the Electrochemical Society, vol. 152, Issue 7, 2005, pp. A1418-A1422.
Pattle, R.E., "Nature", 174, 660, Oct. 2, 1954.
Weinstein, J.N. et al., "Electric Power from Differences in Salinity: The Dialytic Battery", Science 13, vol. 19, No. 4227, Feb. 13, 1976, pp. 557-559.
Brogioli, D. et al., "Exploiting the spontaneous potential of the electrodes used in the capacitive mixing technique for the extraction of energy from salinity difference", Energy & Environmental Science, Issue 12, 2012, pp. 9870-9880.
Olsson, M. et al., "Salinity Gradient Power: Utilizing Vapor Pressure Differences", Science, vol. 206, No. 4417, Oct. 26, 1979, pp. 452-454.
Smithyman, J. et al., "Flexible supercapacitor yarns with coaxial carbon nanotube network electrodes", Materials Science and Engineering: B, vol. 184, 2014, pp. 34-43.
Satterfield, M.B., et al., "Non-Fickian Water Vapor Sorption Dynamics by Nafion Membranes", Journal of Physical Chemistry B, vol. 112, No. 12, 2008, pp. 3693-3704.
Liu, F. et al., "Effect of additional charging and current density on the performance of Capacitive energy extraction based on Donnan Potential", Energy & Environmental Science, Issue 9, 2012, pp. 8642-8650.

Sone, Y. et al., "Proton Conductivity of Nafion 117 as Measured by a Four-Electrode AC Impedance Method", Journal of the Electrochemical Society, vol. 143, Issue 4, 1996, pp. 1254-1259.
Rittersma, Z.M., "Recent achievements in miniaturised humidity sensors—a review of transduction techniques", Sensors and Accuators A: Physical, vol. 96, Issues 2-3, Feb. 28, 2002, pp. 196-210.
Kuban, P. et al., "Durable Microfabricated High-Speed Humidity Sensors", Analytical Chemistry 76, 2004, pp. 2561-2567.
Sun, G. et al., "Humidity response properties of a potentiometric sensor using LaF3 thin film as a solid electrolyte", Review of Scientific Instruments, 82, 2011, pp. 083901-1-083901-4.
Saputra, H. et al., "Solid state, dry zinc/MCM-41/air cell as relative humidity sensor", Journal of Membrane Science, vols. 415-416, Oct. 1, 2012, pp. 237-241.
Sata, T., "Possibility for potentiometric humidity sensor of composite membranes prepared from anion-exchange membranes and conducting polymer", Sensors and Actuators B: Chemical, vol. 23, Issue 1, 1995, pp. 63-69.
Chan, C. et al., "High-performance lithium battery anodes using silicon nanowires", Nature Nanotechnology 3, 2008, pp. 31-35.
Stenina, I.A. et al., "Ion Mobility in Nafion-117 membranes", Desalination, vol. 170, Issue 1, Oct. 25, 2004, pp. 49-57.
Smithyman, J. et al., "Energy harvesting from humidity changes with a flexible coaxial electrode solid-state cell", RSC Adv. 4, 2014, p. 29759-29764.
Smithyman, J. et al., "Flexible supercapacitor yarns with coaxial carbon nanotube network electrudes", Materials Science and Engineering B, 184, 2014, pp. 34-43.
Pushparaj, V. et al., "Flexible energy storage devices based on nanocomposite paper", PANS, vol. 104, No. 34, Aug. 21, 2007, pp. 13574-13577.
Hart, R. et al., "3-D Microbatteries", Electrochemistry Communications 5, 2003, pp. 120-123.
Galtier, J. et al., "How early ferns became trees", Proc. R. Soc. Land. B, 26, 2001, pp. 1955-1957.
Feng, Y. et al., "Wearable Carbon Nanotube Fibers for Energy Storage", International Journal of Electrochemical Science, 7, 2012, pp. 12432-12439.
Jung H. et al., "Liquid metal nanodroplet dynamics inside nanocontainers", Scientific Reports, 3, 2013, pp. 1-7.
Yoo, J. et al., "Ultrathin Planar Graphene Supercapacitors", Nano Letters 11, 2011, pp. 1423-1427.
Samuel, E.I. et al., "Accelerated spheroidisation induced by high intensity electric pulse in a severly deformed eutectoid steel", J. Mater. Res. vol. 25, No. 6, 2010, pp. 1020-1024.
Zhao, Q. et al., "Diffusion and Interfacial Transport of Water in Nafion", The Journal of Physical Chemistry B, 115, 2011, pp. 2717-2727.

* cited by examiner

FLEXIBLE ELECTRICAL DEVICES AND METHODS

CROSS-REFERENCE TO RELATED APPLICATIONS

This application is a divisional of U.S. patent application Ser. No. 14/471,750, filed on Aug. 28, 2014, which claims priority to U.S. Provisional Application No. 61/870,859, filed on Aug. 28, 2013, the disclosures of which are incorporated herein by reference.

TECHNICAL FIELD

The present disclosure is generally related to electrical devices, including but not limited to flexible electrical devices, which may be in a fiber shape, for use as or in energy harvesting devices, capacitors, batteries, fuel cells, sensors, among other applications.

BACKGROUND

Carbon nanomaterials such as carbon nanotubes (CNTs) are useful in electrochemical systems such as fuel cells, batteries, electrochemical capacitors, and electrical energy storage (EES) devices. Fibrous morphologies of carbon nanomaterials offer different capabilities compared to their planar counterparts, particularly for flexible electrochemical devices.

Conventional flexible EES devices with fiber-like geometries are fabricated by twisting the conductive strands (electrodes) together. However a potential drawback associated with this construction is that the twisted electrode fibers may cause non-uniform current and electric potential distributions due to the helical interaction between the two electrodes. Such non-uniform currents can lower cell efficiencies due to the poor utilization of the electrode materials, decrease cycle life because of the detrimental effects of non-uniform stresses on electrode stability, and induce local hot-spots.

It therefore would be desirable to provide new and improved flexible EES or other electrochemical devices that are capable of ameliorating some or all of the foregoing disadvantages. In particular, it would be desirable for the devices to be able to maintain high volumetric energy and power densities during electrochemical device deformations.

SUMMARY

In one aspect, a flexible electrical device is provided. The device includes a coated inner carbon nanotube electrode which has an exterior surface. The device further includes an outer carbon nanotube electrode disposed on the exterior surface of the coated inner carbon nanotube electrode. An overlap region exists where the coated inner carbon nanotube electrode and the outer carbon nanotube overlap one another. The device has a fiber-like geometry and first and second electrode ends.

In another aspect, methods are provided for fabricating an electrical component. In one embodiment, the method includes providing an inner electrode which comprises one or more carbon nanotube fibers; coating the inner electrode with a polymer electrolyte to form a polymer-coated inner electrode having an exterior surface; and attaching an outer electrode, which comprises carbon nanotube sheets, to at least a portion of the exterior surface of the polymer-coated inner electrode, thereby forming a flexible electrical component having a fiber-like geometry.

In yet another embodiment, methods of using the flexible electrical components are provided. In one embodiment, a method of detecting a change in relative humidity is provided, which includes placing a sensing device in a gaseous environment and measuring, via a potentiostat, an open circuit potential to detect and/or measure a change in relative humidity of the gaseous environment. The sensing device has a fiber-like geometry extending between first and second electrode ends and includes an inner carbon nanotube electrode, a polymer electrolyte coating on the inner carbon nanotube, and an outer carbon nanotube electrode covering an exterior surface of the polymer electrolyte-coated inner carbon nanotube electrode, wherein the first and second electrode ends are operably coupled to the potentiostat.

DETAILED DESCRIPTION

Flexible electrical device have been developed that include a coated inner carbon nanotube electrode and an outer carbon nanotube electrode that overlap one another at an overlap region, providing a coaxial electrode design. The inclusion of these carbon nanotube electrodes enables the integration of an electronic conductor and active material of each electrode into a single component. The features of the flexible electrical devices described herein beneficially enable the device to maintain high volumetric energy and power densities during device deformations.

Without being limited to a single theory, a coaxial design of the flexible electrical device permits uniform primary current distribution because of the radial ion transport between electrodes. This radially symmetrical design may be advantageous for the electrochemical properties and may also provide mechanical properties which benefit the development of robust flexible electrical devices. The coaxial design may enable the device's stress response to bending or other deformation to be essentially independent of location due to the symmetric area moment of inertia throughout the cross-section. This may allow for generalized predictions of the stress distributions in response to external forces. Furthermore, the concentric cylinder construction may allow for the ability to tailor the location of different components based on these predicted stress distributions in order to create devices with robust mechanical properties.

Embodiments of the flexible electrical devices described herein have been found to advantageously provide a high energy density. See Example 5 below. Without being bound by a single theory, this high energy density is believed to be, at least in part, the result of the efficient space utilization enabled by device's coaxial structural design and materials of construction. For example, the multifunctionality of the CNT yarn contributes through its high strength, electrical conductivity, and specific surface area, which were found to enable the CNT yarns to function both as the conductive structural support and the active material. Also, CNT networks typically have a more open/interconnected pore structure than that of graphene networks and other microporous carbons. This advantageously minimizes the amount of inactive mass/volume in the device by alleviating the need for supportive substrates or conductive current collectors, and in turn provided an increase in the gravimetric and volumetric properties of the final device.

Figure 1A:
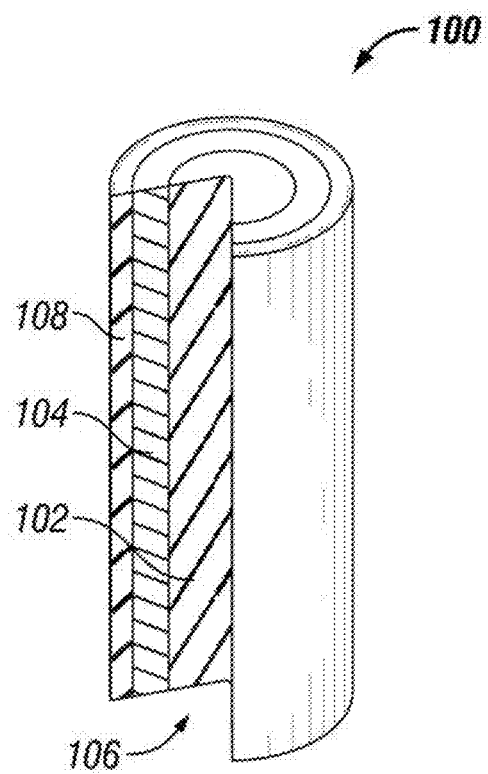
FIG. 1A is a perspective, partial cut-away view of a flexible electrical device in accordance with an embodiment of the present disclosure.
Figure 1B:
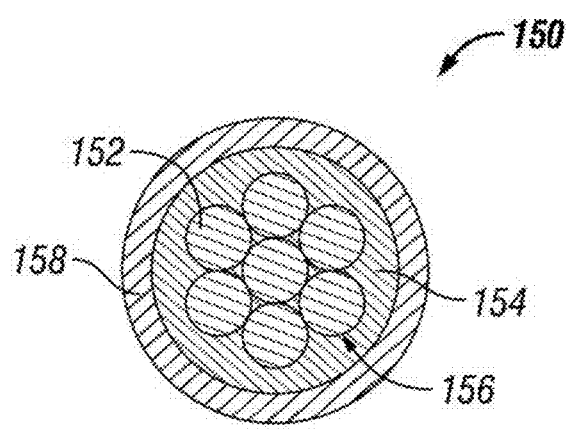
FIG. 1B is a cross-sectional view, in the axial direction, of a flexible electrical device in accordance with an embodiment of the present disclosure.

In embodiments, the flexible electrical device includes a coated inner carbon nanotube electrode with an exterior surface and an outer carbon nanotube electrode disposed on the exterior surface of the coated inner carbon nanotube electrode. Examples of this structure are shown in FIGS. 1A and 1B. In some embodiments, the inner electrode is a monofilament, for example in FIG. 1A. FIG. 1A shows flexible electrical device 100 which has a coaxial design with an inner monofilament electrode 102. The inner electrode 102 is coated with a polymer electrolyte 104 which together form a coated inner electrode 106. The coated inner electrode 106 has an outer surface upon which an outer electrode 108 is coated. In other embodiments, the inner electrode is a multifilament, for example in FIG. 1B. FIG. 1B shows flexible electrical device 150 which also has a coaxial design having an inner multifilament electrode 152. The inner electrode 152 is coated with a polymer electrolyte 154 which together form a coated inner electrode 156. The coated inner electrode 156 has an outer surface which is coated with an outer electrode 158 is surrounded by an outer electrode 112 that includes a layer of carbon nanotube sheets. As shown in these figures, an overlap region exists in the devices wherein the coated inner carbon nanotube electrode and the outer carbon nanotube electrode overlap one another.

The flexible electronic device generally is highly elongated with a very small cross-section in the shorter dimension. That is, in embodiments, the device has a fiber-like geometry. In embodiments, the device includes opposed first and second electrode ends. In particular embodiments, the first and second electrode ends have opposite electrical potentials, either positive or negative, depending on the connections made to form a circuit using the device.

Figure 2:
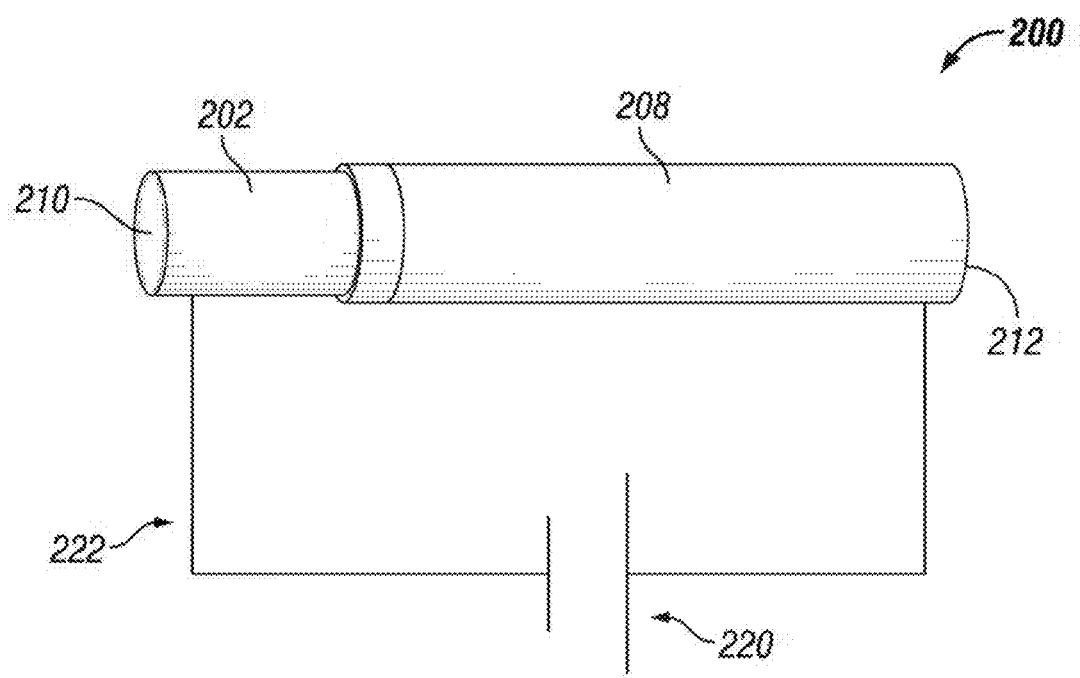
FIG. 2 is a perspective view of a coaxial design of a flexible electrical device in accordance with an embodiment of the present disclosure, as provided within a circuit.

FIG. 2 shows an embodiment in which flexible electrical device 200 includes an inner carbon nanotube electrode 202 and outer carbon nanotube electrode 208. The device 200 is included in an electrical circuit 222, with an external energy device 220, wherein the device is electrically operably connected via first and second electrode ends 210 and 212. As shown, the outer electrode 208 overlaps the inner electrode 202. The overlap may be complete or partial. In some embodiments, the exterior surface of the outer electrode is cylindrical and the overlap region is an elongated cylindrical shape, such that the flexible electrical device is a coaxial electrode. In some embodiments, the overlap region in which the inner electrode and outer electrode overlap one another is from about 20 mm to about 1 km in length, from about 1 cm to about 1 m in length, from about 10 microns to about 10 mm in length, or from about 40 mm to about 5 m. In certain embodiments, the overlap region is about 10 microns to about 3 m in diameter. In other embodiments, the overlap region is from about 40 mm to about 60 mm in length and about 500 microns in diameter. Other overlap dimensions are envisioned.

The flexible devices described herein preferably are configured to be able to undergo flexural deformation with minimal impact on its electrical properties. For example, in certain embodiments, about 95% of the energy density and about 99% of the power density is retained in the flexible device when the device having a fiber-like geometry is wound around a cylinder having a diameter from about 1 mm to about 50 cm.

In some embodiments, the coated CNT inner electrode assembly is wrapped with thin sheets of CNTs, creating a concentric cylindrical outer electrode of porous CNT networks with the CNT inner electrode and polymer electrolyte coating at its center axis. In some embodiments, the coated inner carbon nanotube electrode includes an inner carbon nanotube electrode and an electrolyte coating on the inner carbon nanotube electrode. In some embodiments, the uncoated inner carbon nanotube electrode is one or more filaments of a carbon nanotube yarn. In embodiments in which the uncoated inner carbon nanotube electrode is one or more filaments of a CNT yarn, the CNT yarn acts as the backbone for the flexible electrical device. The CNT yarn of the inner carbon nanotube electrode may function as a structural support, electron conductor, active material, and/or active material support, thereby minimizing inactive mass and volume which maximizes the device properties achievable from a given electrode material.

In some embodiments, the outer electrode includes one or more carbon nanotube sheets. In other embodiments, the inner electrode or outer electrode includes another appropriate material, including but not limited to activated carbon, carbon fiber cloth, carbide-derived carbon, carbon aerogel, graphene, metal oxides, conductive polymers, and combinations thereof.

In a preferred embodiment, the inner and outer electrodes are substantially coaxial. In certain embodiments, a mass of the inner electrode is substantially equal to a mass of the outer electrode. In other embodiments, the outer electrode is attached around a cylindrical-shaped surface of the inner electrode or the coated inner electrode. In still other embodiments, the polymer coated CNT inner electrode is wrapped with thin sheets of CNTs to create a device with a concentric, non-cylindrical outer electrode, but wherein the inner electrode and outer electrode interact as if they are substantially coaxial. In other embodiments, the inner electrode assembly is not wrapped with thin sheets of CNTs and a network of CNTs are formed and/or applied to the polymeric coated inner electrode assembly using other suitable methods.

In embodiments in which the inner carbon nanotube electrode includes CNT yarn, the CNT yarn may also form a supporting structure for the coating thereon. The coating may be any suitable electrolyte capable of being formed onto a layer to cover the exterior layer of the inner carbon nanotube electrode. In some embodiments, electrolyte coating layer is a polymer electrolyte. In certain embodiments, the polymer electrolyte is a PVA polymer incorporated with either $H_3PO_4$ or LiCl. In certain embodiments, the polymer electrolyte comprises a sulfonated tetrafluoroethylene based fluoropolymer-copolymer electrolyte. Other non-limiting examples of suitable electrolytes may include an aqueous acid, an alkali solution or solid, or a salt solution or solid, and combinations thereof.

In some embodiments in which the inner electrode comprises multiple filaments of CNT yarn, an aqueous solution may be used to aid in the adhesion between the filaments and may include the same ions as those in the electrolyte coating of the device. In some embodiments, flexible electrical devices having Li-ion exchanged Nafion polymer electrolytes may use an aqueous solution having LiOH to aid in the adhesion between the filaments. In still other embodiments, water may be used without an added electrolyte to aid in the adhesion between the filaments.

The electrolyte coating may function as a separator of the inner and outer electrodes. In other embodiments, a separator material, different than the electrolyte coating, may be included and used to separate the inner and outer electrodes. Non-limiting examples of such separator materials include a porous polymer membranes (PET, PE, PVC, PS, PP, Nylons or other synthetic or natural polymers), woven glass fibers, porous woven ceramic fibers, and combinations thereof.

In certain embodiments, the total capacitance/capacity (i.e., amount of charge storage) capabilities of the outer electrode is substantially equal to the total capacitance/capacity of the inner electrode. In other embodiments, the total capacitance/capacity (i.e., amount of charge storage) capabilities of the outer electrode is not equal to the total capacitance/capacity of the inner electrode. It should be noted that any number of electrode properties (e.g., mass, volume, porosity, surface area, etc.) may be selected in order to balance the performance capabilities between two electrodes and optimize design.

Figure 21A:
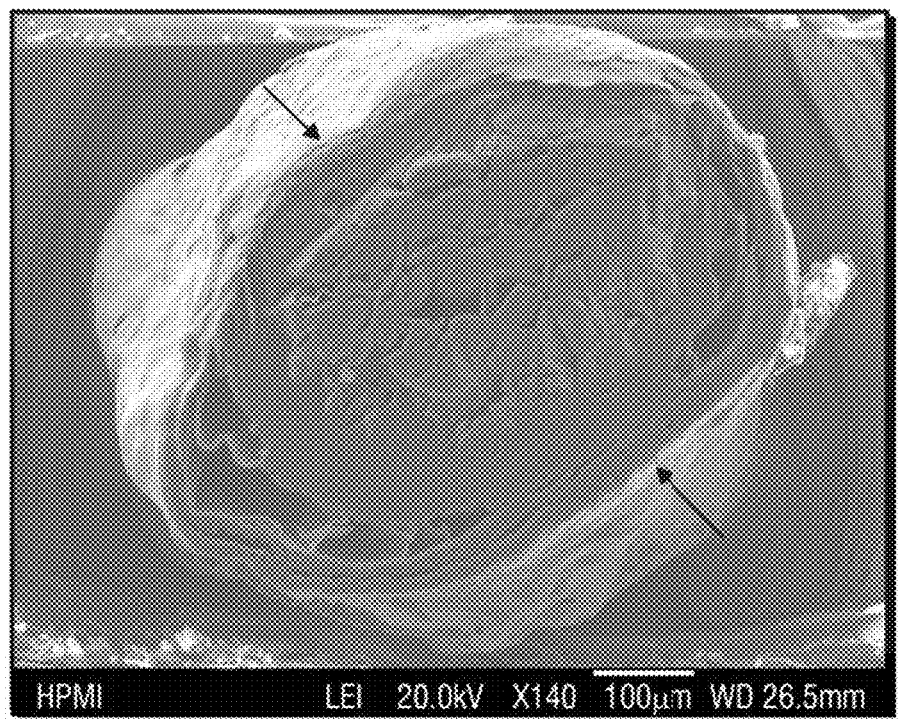
FIGS. 21A-21B are scanning electron micrographs (SEMS) of a cross-section of a coaxial coated electrode having a coating thickness of about 50-60 µm at 100 µm scale (FIG. 21A) and at a 10 µm scale (FIG. 21B).
Figure 21B:
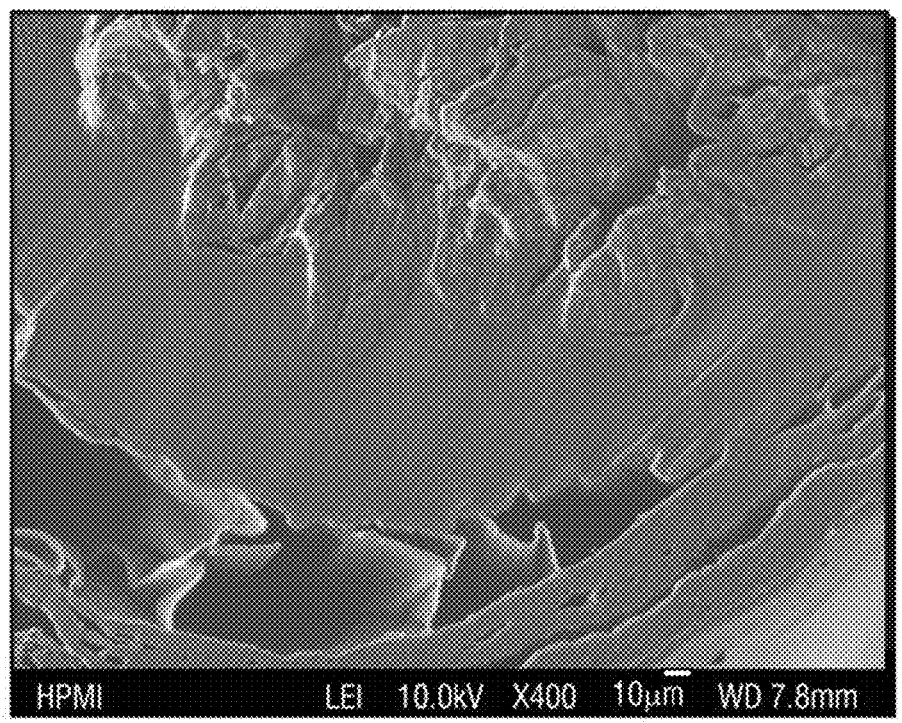
Figure 22A:
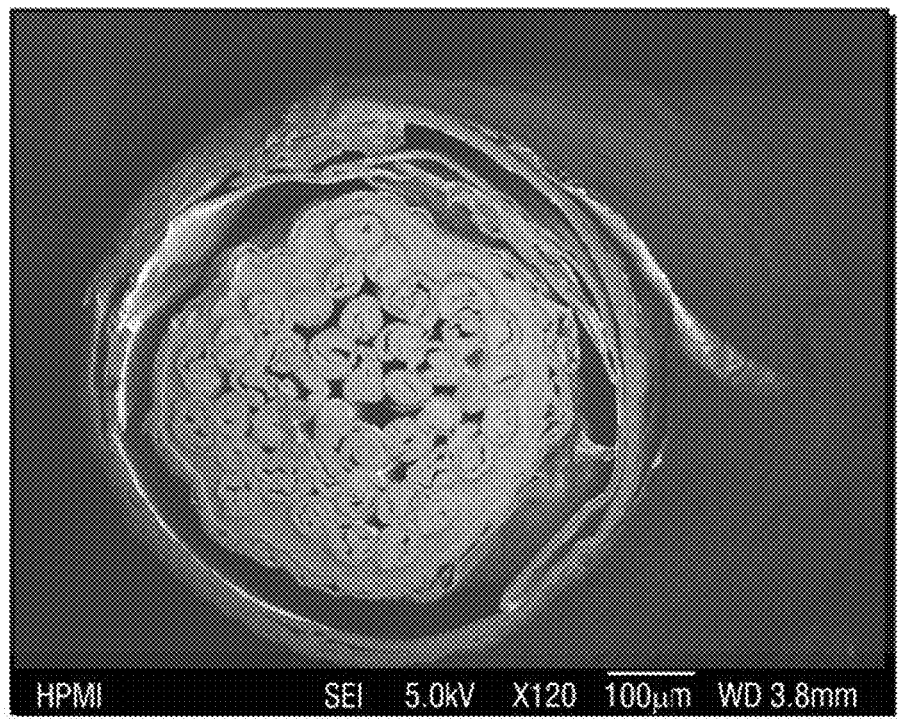
FIGS. 22A-22B are SEMS of a cross-section of a coaxial coated electrode having a coating thickness of about 20-30 µm at 100 µm scale (FIG. 22A) and at a 10 µm scale (FIG. 22B).
Figure 22B:
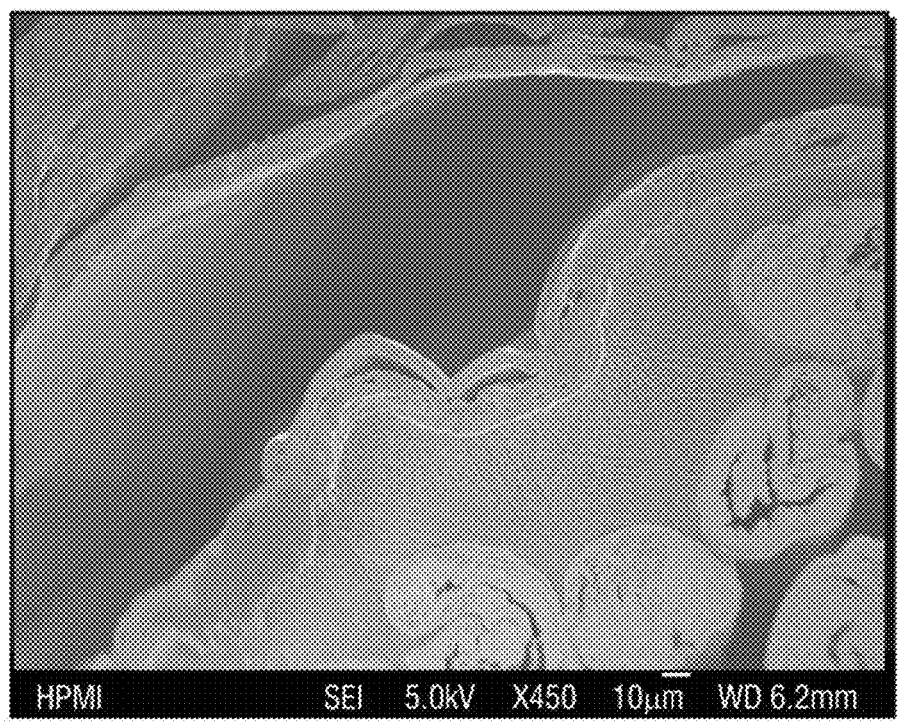

FIGS. 21A-21B show a coaxial electrode, as described herein, having a coating thickness of about 50-60 µm. The arrows indicate the deformation that resulted from the cross-section cut. FIGS. 22A-22B shows another coaxial coated electrode having a coating thickness of about 20-30 µm. Both sets of figures show a multifilament inner electrode with a polymer electrolyte region creating separation from the multi-layer outer electrode. These figures show an intimate contact between the polymer electrolyte and the outer filaments of the inner electrodes and the first layer of the outer electrodes. While not being limited to any particular theory, it is believed that the high quality interface between the components of the flexible electrical devices helps achieve the robust mechanical and electrochemical properties of these devices.

In certain embodiments, one or more of the flexible devices described herein may be configured as an energy storage device, a sensor device, or an energy harvesting device. In some embodiments, an energy storage device is provided that includes one or more of the flexible electrical devices described herein. In other embodiments, a sensor device is provided that includes one or more of the flexible electrical devices described herein. In yet other embodiments, an energy harvesting device is provided that includes one or more of the flexible electrical devices described herein.

Device Fabrication

The flexible devices describe herein may be made and assembled by any suitable method. In one embodiment, the method includes providing an inner electrode which comprises one or more carbon nanotube fibers; coating the inner electrode with a polymer electrolyte to form a polymer-coated inner electrode; and the securing a second, outer electrode, which includes carbon nanotube sheets, onto at least a portion of the exterior surface of the polymer-coated inner electrode. The securing may be coating, adhering, wrapping or any other suitable means for providing the second electrode material onto the coated inner electrode. The materials are selected and dimensioned such that the resulting electrical component is flexible and has a fiber-like geometry.

In some embodiments, before the coating, the inner electrode is at least partially submerged in an electrolyte solution while an electrical charge is applied across the inner electrode. In some embodiments, before attaching the outer electrode, the polymer electrolyte may be dried in open air, under an inert atmosphere, at reduced pressures, at elevated temperatures, or using combinations of these techniques to yield a uniform solid polymer coating on the inner electrode. In other embodiments, the exterior surface of the polymer-coated inner electrode comprises a cylindrical surface. In yet other embodiments, the polymer electrolyte is a gel and the flexible electrical component is configured as a flexible electrical energy storage device. In some embodiments, the gel may be a polyvinyl alcohol (PVA) and phosphoric acid ($H_3PO_4$) polymer gel electrolyte. In other embodiments, other suitable polymer gel electrolytes may be used.

The step of attaching the outer electrode onto or around the cylindrical surface of the coated inner electrode includes forming an overlap region. In some regions, however, the outer electrode does not cover a portion of the cylindrical surface, such that the overlap is not complete, and one or more areas of the cylindrical surface of the inner electrode are exposed, for example, at the ends. The ends may be electrically coupled into an electrical circuit. In one embodiment, the flexible electrical device has a first end and an opposed second end, and the ends are connected to wiring in a circuit by application of a silver paste, silver paint, or other conductive material to the first and/or second electrode ends. Non-limiting examples of suitable conductive material include copper, gold, platinum, palladium, rhodium, iridium, or aluminum pastes and combinations thereof.

In certain embodiments, the method for fabricating an electrical component may include connecting a first measurement contact to a surface of the inner electrode and connecting a second measurement contact to a surface of the outer electrode, in which the flexible electrical component is configured as a flexible sensing device. In certain embodiments, the polymer electrolyte may include a sulfonated tetrafluoroethylene based fluoropolymer-copolymer electrolyte, for example a Nafion® electrolyte. In other embodiments, the first and second measurement contacts may be operably connected to a potentiostat.

Uses of the Devices

The observed performance results of the flexible electrical devices described herein, e.g., high volumetric energy and power densities, the robustness of the energy storage capabilities resistance to deformation, demonstrate the feasibility and attractiveness for these devices in areas such as, energy harvesting devices, capacitors, batteries, fuel cells, and sensors.

Figure 20:
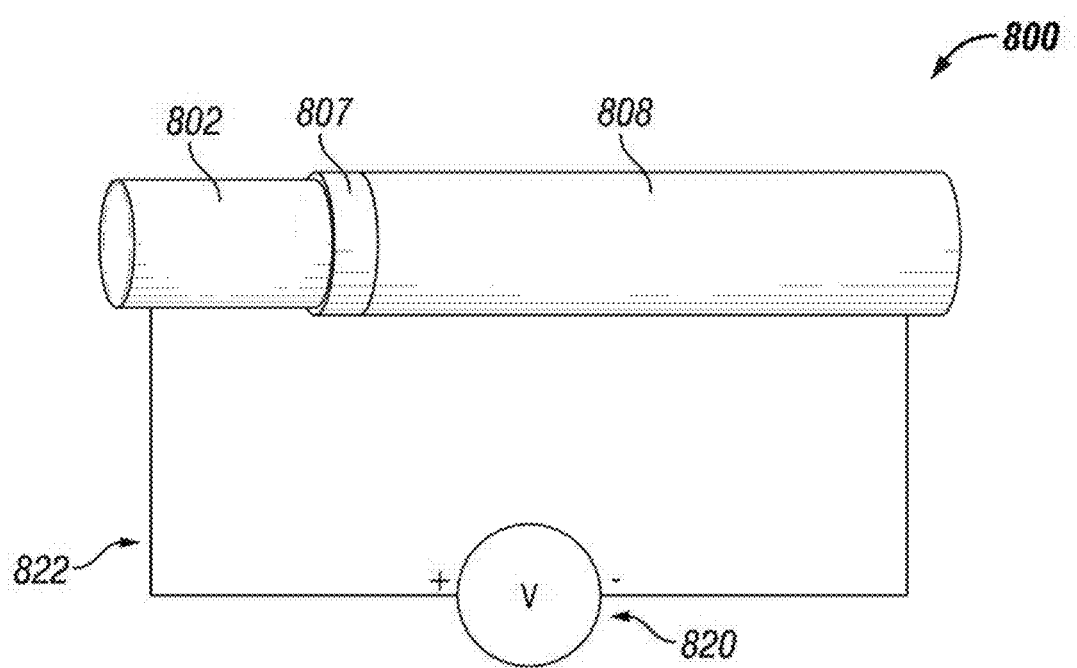
FIG. 20 is a perspective view of a coaxial design of a flexible electrical device in accordance with an embodiment of the present disclosure, with an external circuit suitable for use in measurement of the device's open circuit potential (OCP).

As described herein, the high electrical conductivity, good mechanical properties, and large specific surface area of CNT yarns may enable its multifunctional role as an active electrode material, electrical conductor, and support structure for an entire flexible electrical device. One embodiment of a coaxial fiber cell 800 is shown in FIG. 20. Device 800 includes an inner carbon nanotube electrode 802 and outer carbon nanotube electrode 808, with a polymer electrolyte coating 807 positioned therebetween (e.g., coated onto the inner CNT electrode). The device 800 is included in an electrical circuit 822 with voltmeter 820 suitable for measuring the cell's open circuit potential (OCP).

In certain embodiments, the flexible electrical device is configured as a sensing device for use in detecting a change in relative humidity of a gaseous environment. For example, in some embodiments, a method of detecting a change in relative humidity of a gaseous environment may include placing a sensing device in the gaseous environment and measuring, via a potentiostat, an open circuit potential to detect and/or measure a change in relative humidity of the gaseous environment. In some embodiments, the method is used to detect changes in relative humidity in the gaseous environment with a relative humidity in the range of about 5% to about 95%. In other embodiments, the flexible electrical device is configured as an energy harvesting device.

It has been discovered that a potential difference across a polymer electrolyte that contains substantially fixed ions exists, where the concentration gradient is established due to an increase or decrease in the local water content of the outer electrode. This local concentration change occurs due to the hygroscopic nature of the polymer electrolyte and its ability to rapidly exchange $H_2O$ molecules with the surrounding environment as the relative humidity changes. The occurrence of this absorption/desorption at only one of the electrodes establishes the concentration gradient and is achieved through the use of a coaxial electrode according to the present disclosure. The coaxial architecture helps ensure that the inner electrode is shielded from the surrounding environment, thereby causing the water absorption/desorption to occur only at the outer electrode.

An open-circuit potential response is generated when a change in the relative humidity occurs in the environment surrounding a flexible electrical device composed of coaxial carbon nanotube (CNT) network electrodes and a polymer electrolyte. The change in humidity may induce a corresponding change in the water content in the electrolyte near the outer electrode as water is absorbed or evaporated. The resulting water concentration gradient in the ionic polymer electrolyte between the two electrodes generates a Gibbs free energy that is measurable in the open-circuit potential (OCP) of the device. This suggests the Gibbs free energy as the source of the OCP response.

The characteristics of the OCP response is determined by the difference between the rate of change of the water content at one electrode and that of the opposite electrode. At the outer electrode, this change rate is determined by the rate of the humidity change, the absorption/evaporation rate and the rate at which water diffuses to/from the electrode. Since the coaxial electrode architecture shields the inner electrode from the surrounding environment, the rate of water diffusion through the electrolyte will determine the rate of change of the water content at inner electrode. Thus, the method of detecting a change in relative humidity of a gaseous environment using a sensing device, as described herein, exploits the hygroscopic properties of the polymer electrolyte and utilizes changes in the relative humidity of the surrounding environment to induce a measurable concentration gradient between the electrodes.

Furthermore, the concentration gradients, relative humidity change, and $H_2O$ absorption/desorption demonstrate the ability of the flexible electrical devices, as described herein, to "harvest" the chemical potential energy that is known to exist in ionic concentration gradients by utilizing changes in the relative humidity. When that happens, and the voltage and/or current is produced, that is "energy generation." Upon that generation, the device also has the ability to store that energy for some period of time (i.e., the voltage of the cell and it's time decay). This is because the cell/electrodes may also function as an energy storage device. Thus, this aspect may be considered the "energy harvesting" (harvesting/storage of the electrical energy that is generated). In addition, the design/fabrication of the electrode, which enables the voltage to be produced in the first place, may also be considered harvesting (harvesting of the potential chemical energy that exists in the ionic concentration gradients).

The flexible electrical device and methods may be further understood with the following non-limiting examples.

Example 1: Preparation of a Flexible Electrical Device

CNT yarns and nonwoven CNT sheets (Nanocomp Technologies, Inc.) underwent a mild purification process to remove catalyst particles, amorphous carbons, and residual resins and/or other contaminants. The mild purification process included a 400° C. heat treatment in a tube furnace with both ends of the tube open to the atmosphere. Following the heat treatment the samples were soaked in a solution comprising 1 M HCl and a 3:1 mixture of 1 M $H_2SO_4$ and 1 M $HNO_3$. All electrochemical characterization was conducted with a VersaSTAT3-400 potentionstat with an FRA upgrade (Princeton Applied Research). An Olympus BX40 optical microscope with CCD camera was used to measure the device diameter.

A polyvinyl alcohol (PVA) and phosphoric acid ($H_3PO_4$) polymer gel electrolyte was prepared using a suitable method and functioned as both the electrolyte and the electrode separator. The inner electrode was comprised of multiple filaments of a CNT yarn. The filaments were twisted together using small amounts of an aqueous solution, comprising an aqueous solution of $H_3PO_4$, to aid in the adhesion between the yarns. After drying overnight, a ~2 cm region at one end of the multifilament strand was coated with silver paste to form a region for electrical connection.

Prior to coating the inner carbon nanotube electrode with the polymer electrolyte gel, a pre-charging procedure was performed on the inner electrode. While submerged in a 1 M $H_3PO_4$ electrolyte solution, a 0.7 V (vs. SCE) constant potential was applied for about 500 seconds, after which the electrode was immediately removed from the electrolyte solution. The pre-charged electrode was then coated with the $PVA/H_2O/H_3PO_4$ solution using several iterations of dip coating and manual re-twisting which removed excess gel from the strands. After drying overnight in open air, a uniform solid polymer coating was obtained on the inner carbon nanotube electrode.

An outer carbon nanotube electrode was then applied by wrapping thin CNT sheets (about 1 μm thickness or less) around the polymer-coated inner carbon nanotube electrode. The thin CNT sheets were obtained by carefully removing thin layers from purified nonwoven sheet. These removed layers were freestanding and semi-transparent and had a very low density. The sheets were wrapped around the coated inner carbon nanotube electrode, starting about 2 cm from one end and extending past the opposite end of the electrode. The excess was twisted upon itself into a yarn like strand and extended ~2 cm past the end of the inner electrode and coated with silver paint. The total mass of the outer electrode was matched to the total mass of the inner electrode (coated or uncoated). A second application of the polymer electrolyte solution was then used to coat the outer carbon nanotube electrode. The active region of the device (the region in which the two electrodes overlapped one another) was about 40 mm to about 60 mm in length and about 500 microns in diameter. The volume of this active region was used to calculate the volumetric properties of the device.

Example 2: Half-Cell Testing of the Inner Electrodes

Half-cell testing was conducted on the inner carbon nanotube electrode made in Example 1 in an aqueous electrolyte solution of 1 M phosphoric acid ($H_3PO_4$) to establish a baseline. Three electrode half-cell tests were performed with about 40 mm of the inner electrode submerged in the electrolyte solution. Measurements were conducted versus a platinum wire counter electrode using an SCE reference.

Figure 3:
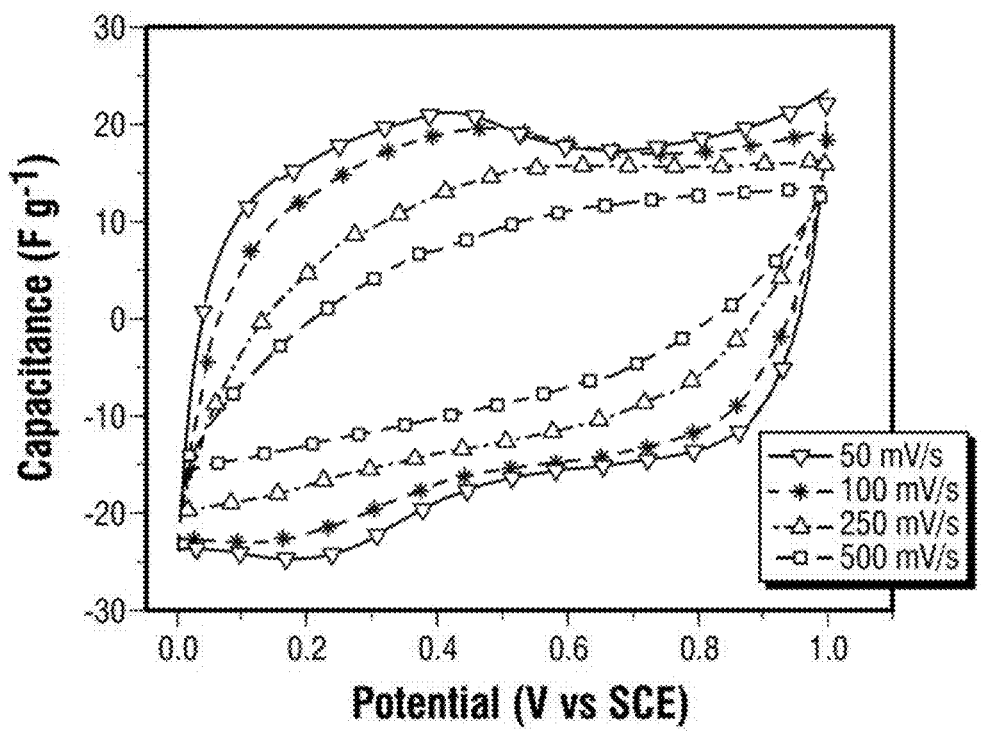
FIG. 3 is a graph of capacitance (F g$^{-1}$) vs. electrical potential (V) and depicts the effects of different scan rates on the half-cell differential capacitance of a multifilament inner electrode in accordance with embodiments of the present disclosure. Voltage is measured and recorded by reference to a saturated calomel electrode (SCE).

FIG. 3 shows the effect of increasing the scan rate on the cyclic voltammetry (CV) signal response. Little change in the differential capacitance was observed between scan rates of about 50 mV $s^{-1}$ to about 100 mV $s^{-1}$. However, at scan rates above 250 mV $s^{-1}$ the CV curves began to lose their rectangular shape, suggesting a deviation from ideal capacitive behavior.

Figure 4:
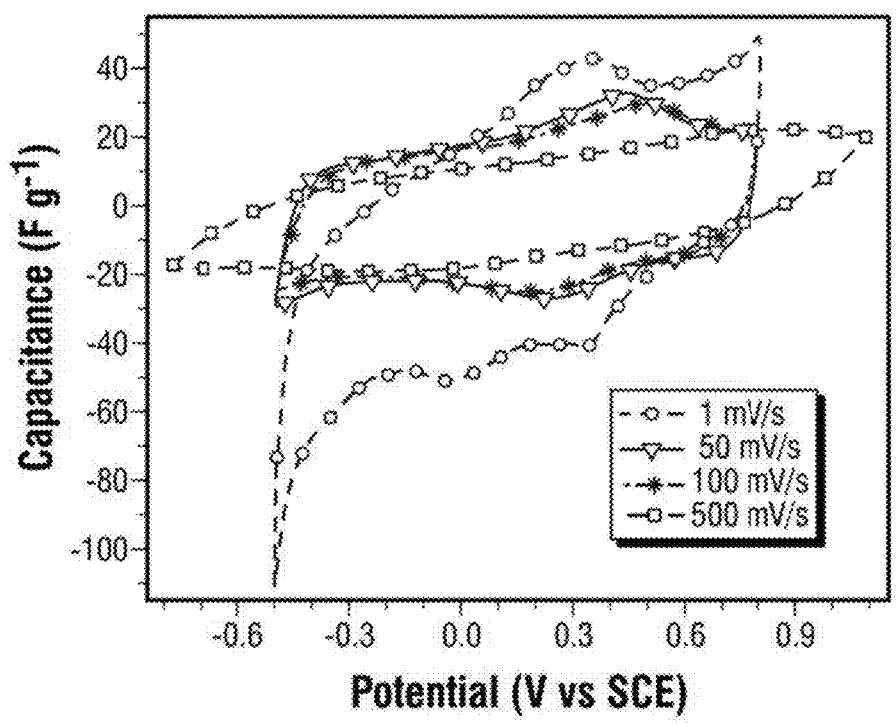
FIG. 4 is a graph of capacitance (F g$^{-1}$) vs. electrical potential (V) and depicts the effects of overpotential on the stability of the electrolyte observed over a wide electrical potential window in accordance with an embodiment of the present disclosure. Voltage is measured and recorded by reference to SCE.

FIG. 4 shows the effect of the scan rate over the window of stability of the electrolyte solution. The CNT yarn was cycled at about 50 mV $s^{-1}$ and about 100 mV $s^{-1}$ in the stable potential window of −0.5 V to 0.8 V (vs. SCE) with no sign of electrolyte decomposition or electrode corrosion. However, when a low scan rate of about 1 mV $s^{-1}$ was used, the stable potential window decreased significantly. Similarly, when the scan rate was increased to 500 mV $s^{-1}$ the potential window was increased to about −0.8 V to 1.1 V with no evidence of electrolyte instability.

To further compare the effects of the potential range, the capacitance and energy density were calculated for each CV test. The integral capacitance ($C_{int}$) of the CV curves were calculated using Equation 1:

$$C_{int} = \frac{\oint \frac{I}{2v} d\psi}{\psi_{max} - \psi_{min}}$$

where I was the measured current density, $\psi$ was the imposed electric potential, $v$ was the scan rate and $\psi_{max}$ and $\psi_{min}$ were respectively the maximum and minimum values of the electric potential and $\omega_{max} - \psi_{min}$ is equal to the voltage window, $\Delta V$. The energy output energy E is then calculated using Equation 2:

$$E = \frac{1}{2} \Delta V^2 C_{int}$$

The synergistic effect of the increased potential window on energy density with CNT electrodes was apparent from the results, as detailed in Table 1 below. Not only did the energy increase by the square of the electric potential, but also the inherent capacitance of the CNT electrode increased with an increasing potential window due to the electrochemical doping effect.

TABLE 1

Capacitance and energy density for multifilament CNT yarn electrodes at different scan rates.

|  | Scan rate (mV s$^{-1}$) | $\Delta V$ (V) | $C_{int}$ (F g$^{-1}$) | Energy (Wh kg$^{-1}$) |
|---|---|---|---|---|
| FIG. 3 | 50 | 1 | 17.6 | 2.44 |
|  | 100 | 1 | 15.8 | 2.19 |
|  | 250 | 1 | 12.3 | 1.71 |
|  | 500 | 1 | 9.60 | 1.33 |
| FIG. 4 | 1 | 1.3 | 33.6 | 7.76 |
|  | 50 | 1.3 | 20.6 | 4.85 |
|  | 100 | 1.3 | 19.2 | 4.50 |
|  | 500 | 1.9 | 13.6 | 6.78 |

Figure 5:
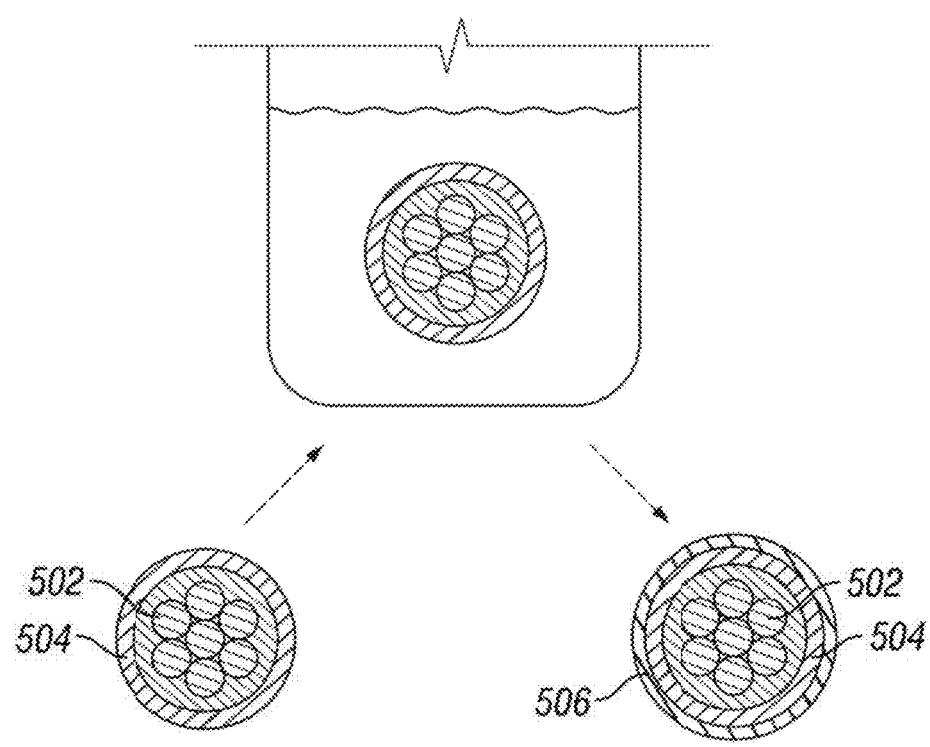
FIG. 5 is a schematic diagram showing a flexible device without an outer polymer electrolyte coating, in a PVA/H$_2$O/H$_3$PO$_4$ electrolyte solution, and following evaporation of excess H$_2$O and gelation of an outer electrolyte coating that is obtained from the electrolyte solution, in accordance with embodiments of present disclosure.

Example 3: Effects of the Outer Electrolyte Coating on the Electrochemical Properties Cyclic voltammetry and electrochemical impedance spectroscopy tests were conducted on the device of Example 1 at various stages of the fabrication process. FIG. 5 shows a schematic representing the three stages of the fabrication process in which the device was tested. In a first stage, i.e., before the outer electrode 504 was coated with a final polymer electrolyte layer 506, after the application but prior to gelation of this outer coating 506, and (c) after gelation of the outer electrode coating 506. A custom fixture was fabricated to allow characterization of the device while it was submerged in a reservoir with sufficient PVA/H$_2$O/H$_3$PO$_4$ solution to ensure gelation did not occur during the experiments.

Figure 6A:
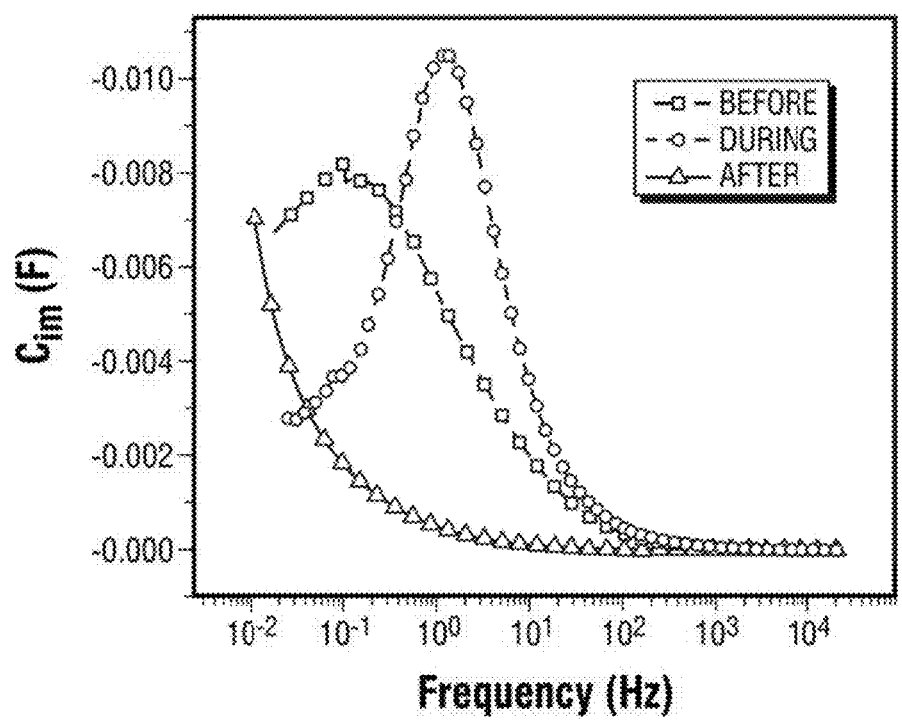
FIG. 6A is a graph of the capacitance ($C_{im}$(F)) vs. frequency (Hz) observed before, during, and after the electrodes of a flexible electrical device, in accordance with the embodiments of the present disclosure, are in the polymer electrolyte solution.
Figure 6B:
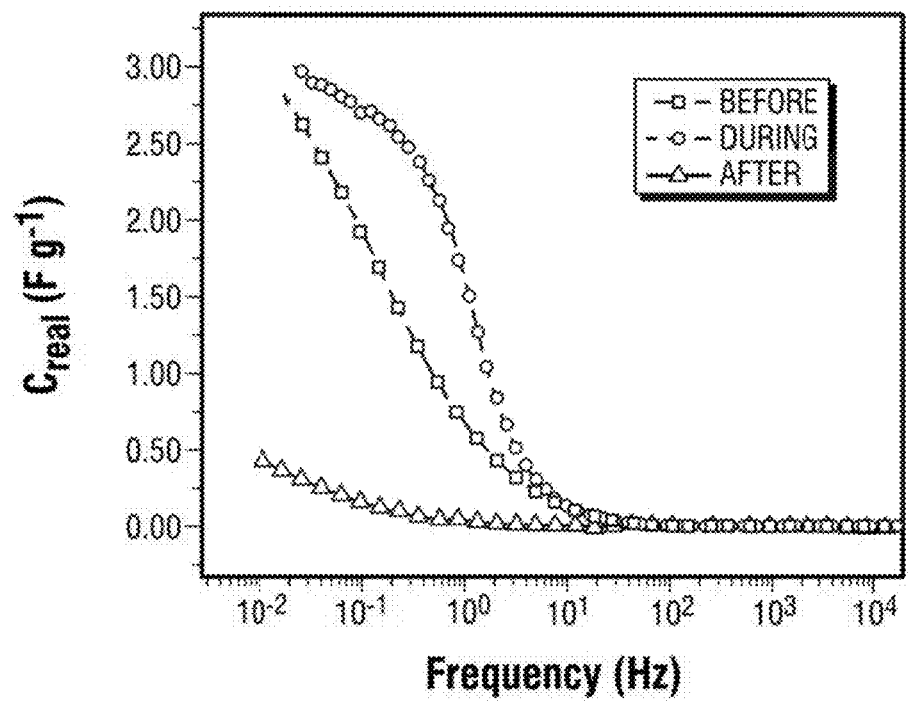
FIG. 6B is a graph of the differential capacitance based on total active mass ($C_{real}$(Fg$^{-1}$)) vs. frequency (Hz) observed before, during, and after the electrodes of a flexible electrical device, in accordance with the embodiments of the present disclosure, are in the polymer electrolyte solution.

Analysis of the complex capacitance results is presented in FIGS. 6A and 6B and provides a convenient method to compare the effects of both the rate and the total amount of charge storage observed for each of the three stages. In FIG. 6A, the location of the imaginary capacitance peaks showed the superior rate capabilities of the device when in the polymer solution (during). The imaginary capacitance peak was located just above 1 Hz when the device is in the gel solution (during), and this peak shifted down to below 0.1 Hz for the device with no outer coating (before). The total capacitance is proportional to the area under the imaginary capacitance peak.

In FIG. 6B, the overall amount of charge storage obtainable from the device with no outer coating (before) was nearly equal to the amount of charge storage observed when the device was submerged in the PVA/H$_2$O/H$_3$PO$_4$ solution (during). The capacitance response of the device with no outer coating (before) and of the device submerged in the solution (during) began at around 10 Hz, and after a rapid increase, the maximum capacitance achieved was nearly equal for both devices. A decrease in capacitive properties was observed after solidification of the outer gel electrolyte layer (after), as the final device capacitance decreased to about 0.5 F g$^{-1}$ from about 3 F g$^{-1}$. Thus, prior to the gelation, the performance of the device while submerged in the electrolyte solution showed excellent charge storage characteristics.

Figure 7A:
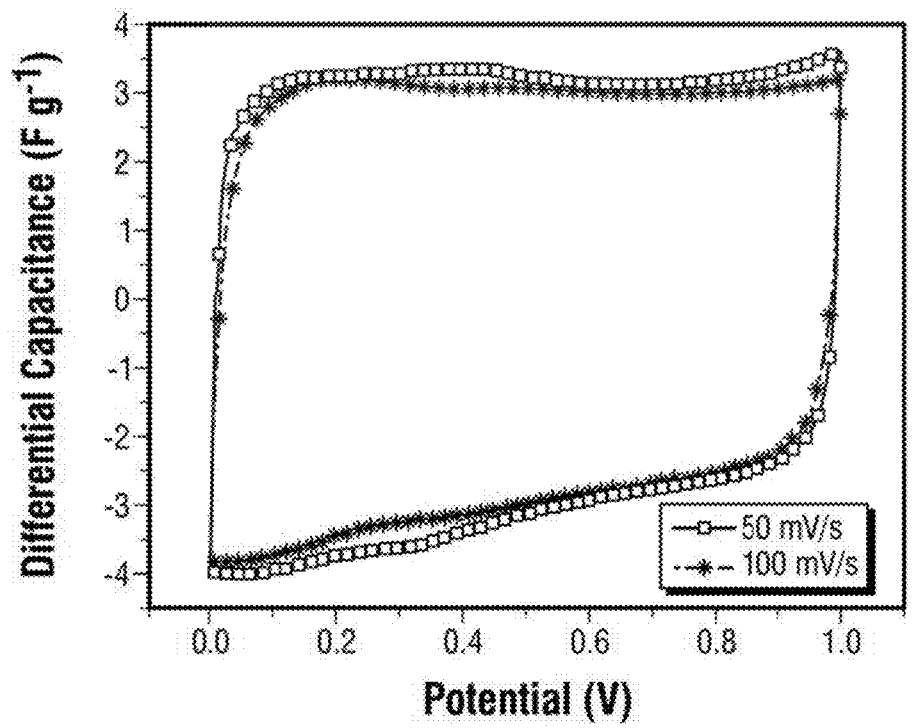
FIG. 7A is a graph of differential capacitance (F g$^{-1}$) vs. potential (V) for both a 100 mV s$^{-1}$ and a 50 mV s$^{-1}$ scan rate of a flexible electrical device, in accordance with an embodiment of the present disclosure, submerged in a PVA/H$_2$O/H$_3$PO$_4$ solution.
Figure 7B:
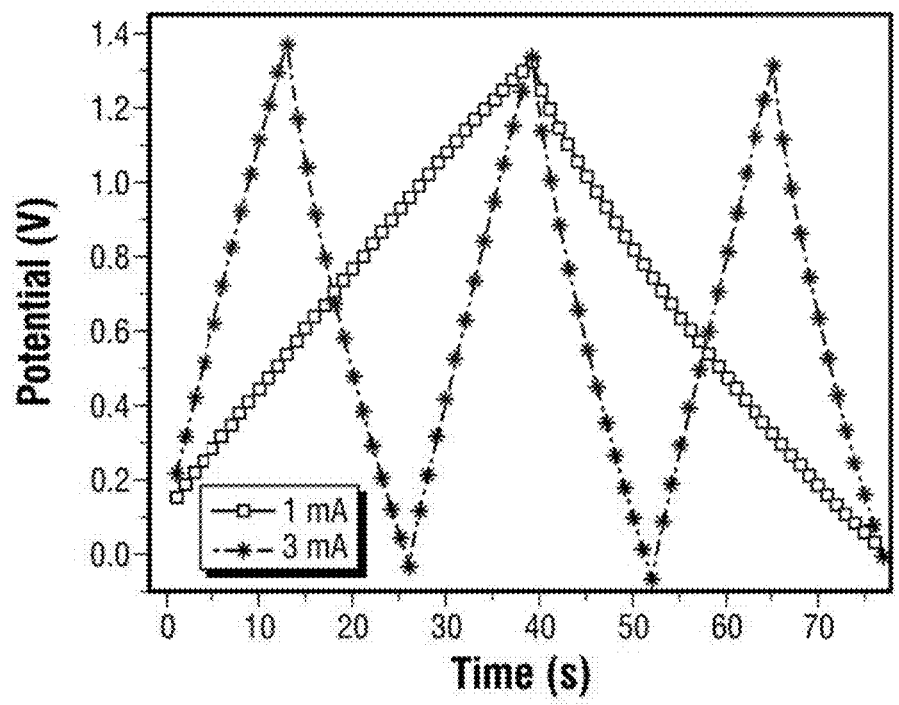
FIG. 7B is a graph of potential (V) vs. time (s) for charge-discharge tests using each of a 1 mA and a 3 mA constant current that correspond to 111 mA g$^{-1}$ and 333 mA g$^{-1}$ current densities, respectively (based on combined mass of the two electrodes) of an flexible electrical device, in accordance with an embodiment of the present disclosure, submerged in a PVA/H$_2$O/H$_3$PO$_4$ solution.

The CV and charge-discharge results in FIGS. 7A and 7B show the characteristic capacitive responses of rectangular CV curves and symmetric galvanostatic charge/discharge voltage profiles.

The integral capacitance ($C_{int}$) of the CCCD test was calculated from the length of time ($\Delta t$) it takes the constant current (I) to discharge the cell from the maximum potential ($\psi_{max}$) to the minimum potential ($\psi_{min}$) using Equation 3:

$$C_{int} = \frac{I \Delta t}{\psi_{max} - \psi_{min}}$$

The energy density was obtained as previously described, using the integral capacitance in Equation 2, while the maximum power was calculated from Equation 4, where V was the voltage and $R_{ESR}$ was the cell resistance calculated from the ohmic drop of the discharge curve.

$$P_{max} = \frac{V^2}{4 R_{ESR}}$$

The gravimetric energy and power densities were calculated based on the total mass of the electrodes in order to compare the performance of the electrodes in the coaxial construction with the performance of prismatic CNT electrodes used in traditional cell designs. At a current density of about 333 mA g$^{-1}$ the energy and power density were about 0.71 Wh kg$^{-1}$ and about 1.4 kW kg$^{-1}$, respectively.

These results demonstrated that the coaxial device was capable of providing electrochemical energy storage with excellent rate capabilities. In some embodiments, the coaxial device was capable of providing electrochemical energy storage with excellent rate capabilities when sufficient water molecules are present within the electrolyte to facilitate the diffusion of electrolyte ions. In other embodiments, electrolytes that maintain a higher solvent concentration can be used to provide substantial improvements to the performance of flexible electrical devices.

Example 4: Effects of Bending on the Electrochemical Properties

Electrochemical impedance spectroscopy (EIS) and constant current charge-discharge (CCCD) studies were also conducted on a flexible electrical device, made by the same fabrication process as the device in Example 1, while applying a constant bending deformation to the device. A marking pen was used as a cylindrical substrate around which one of the flexible electrical devices was wrapped into a spiral wound configuration. The marker had an 11 mm diameter, providing a 5.5 mm radius of curvature.

Figure 8:
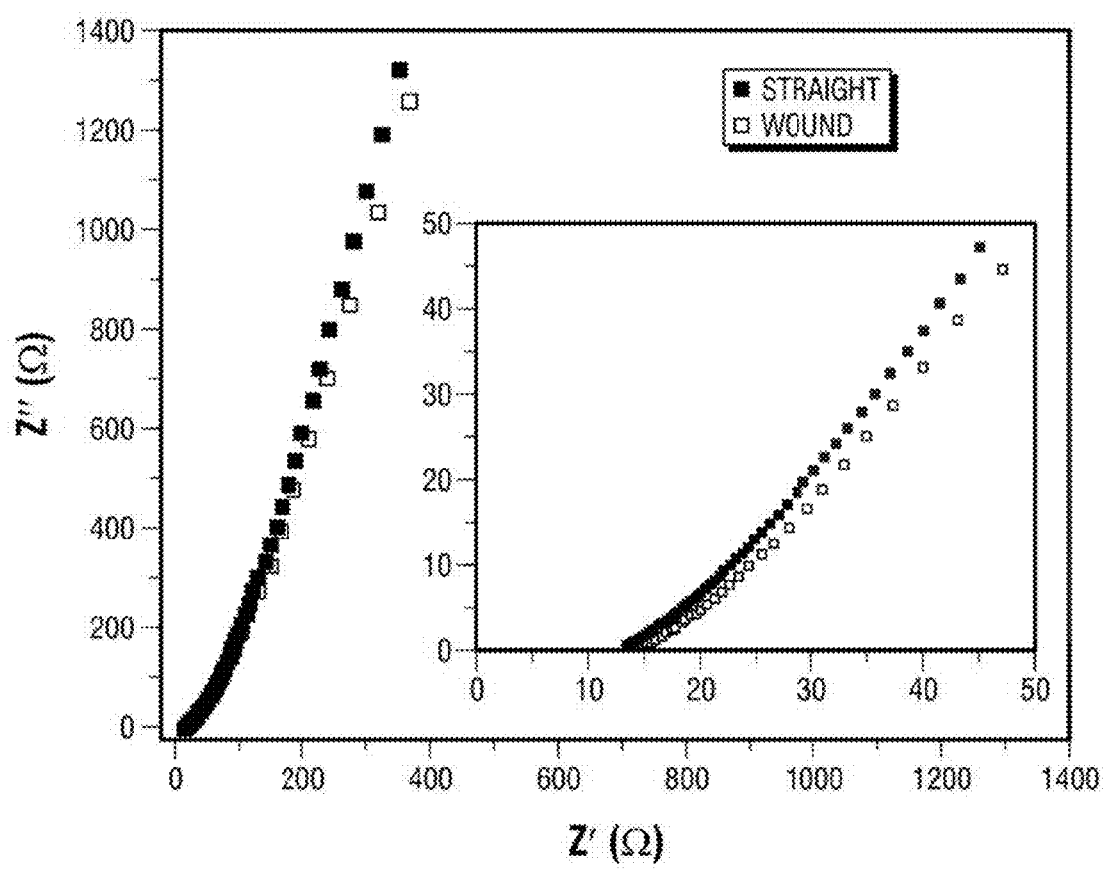
FIG. 8 is a Nyquist plot of a flexible electrical device in both straight and wound configurations, in accordance with embodiments of the present disclosure. The equivalent series resistance (ESR) was 11Ω for the straight configuration and 13Ω for the wound configuration.

Only a minimal difference in the EIS results was observed between the straight configuration of the device and the wound configuration of the device. The Nyquist plots of FIG. 8 for the straight and wound configurations showed plots that lay nearly on top of one another with the wound configuration showing slightly higher impedances, with the difference in impedance response increasing with decreasing frequency. In the higher frequency region the equivalent series resistance (ESR) of the device increased from about 11Ω when in the straight configuration to about 13Ω when the device was in the wound configuration.

Figure 9:
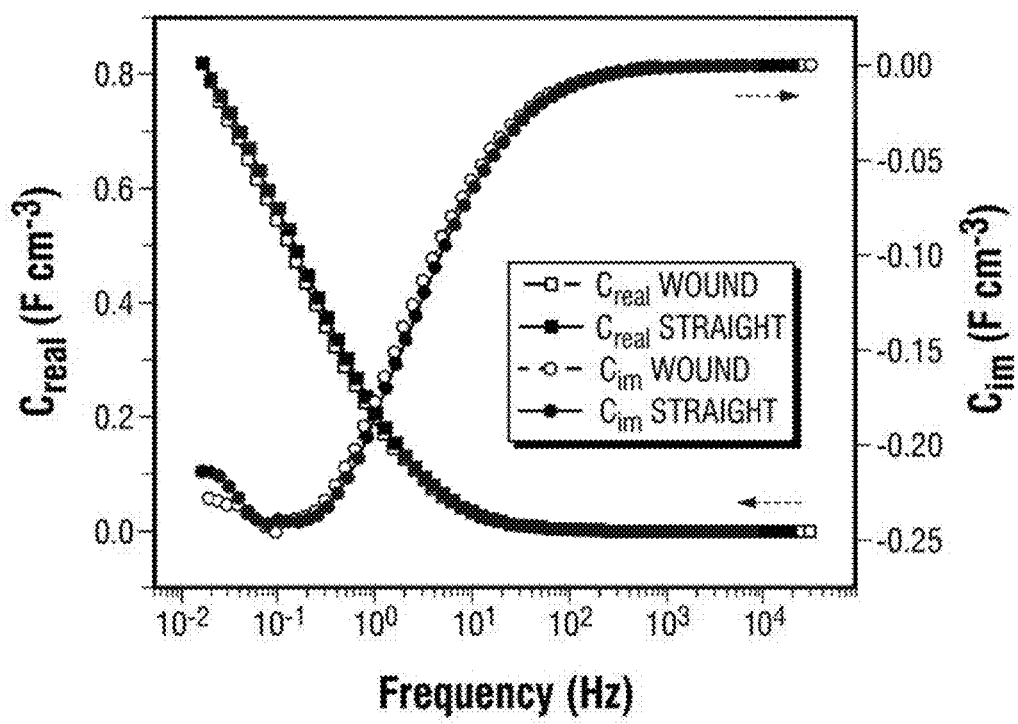
FIG. 9 is a graph of the differential capacitance based on total active mass ($C_{real}$(F cm$^{-3}$)) vs. frequency (Hz) and capacitance ($C_{im}$(F cm$^{-3}$)) vs. frequency (Hz) of the complex capacitance obtained from the EIS tests of the straight and wound flexible electrical devices, according to embodiments of the present disclosure.

The complex capacitance results are shown in FIG. 9 and show the overall stability of the electrochemical properties during bending. In both tests, EIS and CCCD, the real capacitance was greater than about 0.8 F cm$^{-3}$ and the imaginary capacitance peak occurred around 0.15 Hz. The tail of the $C_{im}$ peak began to increase for the wound device, which may indicate higher leakage current when it was bent. Without being bound to a single theory, it was possible that the bending deformation created localized regions of decreased spacing between the electrodes, which may have resulted in higher leakage currents.

Figure 10:
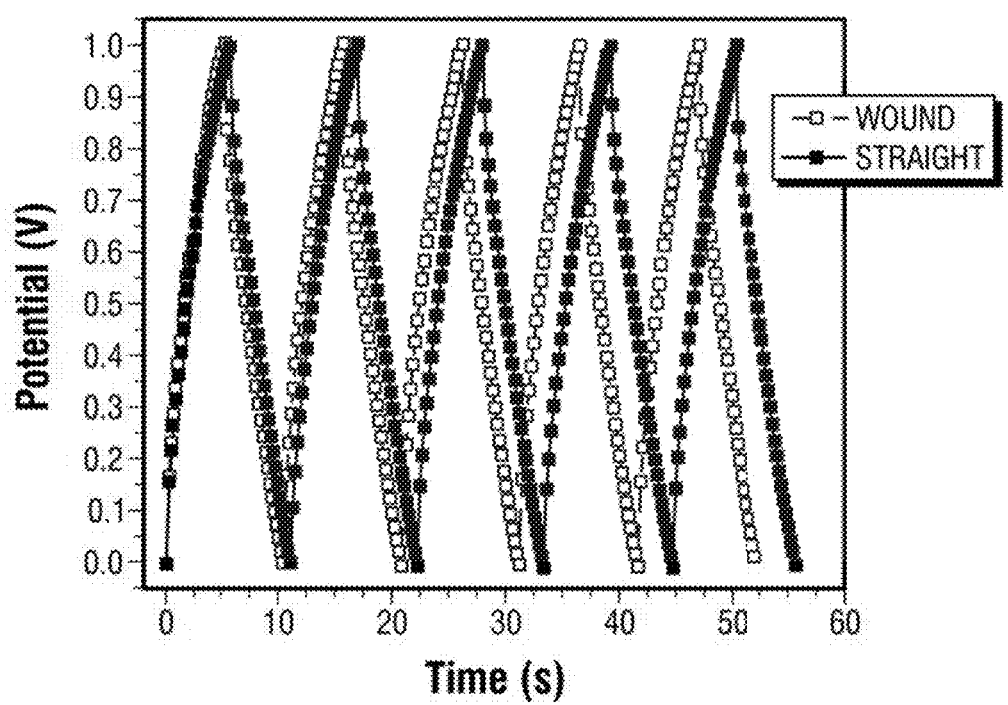
FIG. 10 is a graph of potential (V) vs. time (s) for the first five cycles of a constant current charge-discharge test on the straight and wound flexible electrical devices, in accordance with embodiments of the present disclosure. The current density was 127 mA cm$^{-3}$ based on the total device volume.

FIG. 10 shows the first five cycles of a galvanostatic charge-discharge test for both the straight and wound configurations of the device. The slightly higher resistance of the wound configured device was also evident as the charge-discharge curve began to trail that of the straight configured device as the galvanostatic cycling progressed. The integral capacitance calculated from the discharge curve using Equation 3 and avoiding the ohmic drop (~0.12 V) was about 0.77 F cm$^{-3}$ and about 0.74 F cm$^{-3}$ for the straight and wound configurations, respectively. These results are in agreement with the results of the EIS test.

Example 5: Performance of a Flexible Electrical Device

Figure 11:
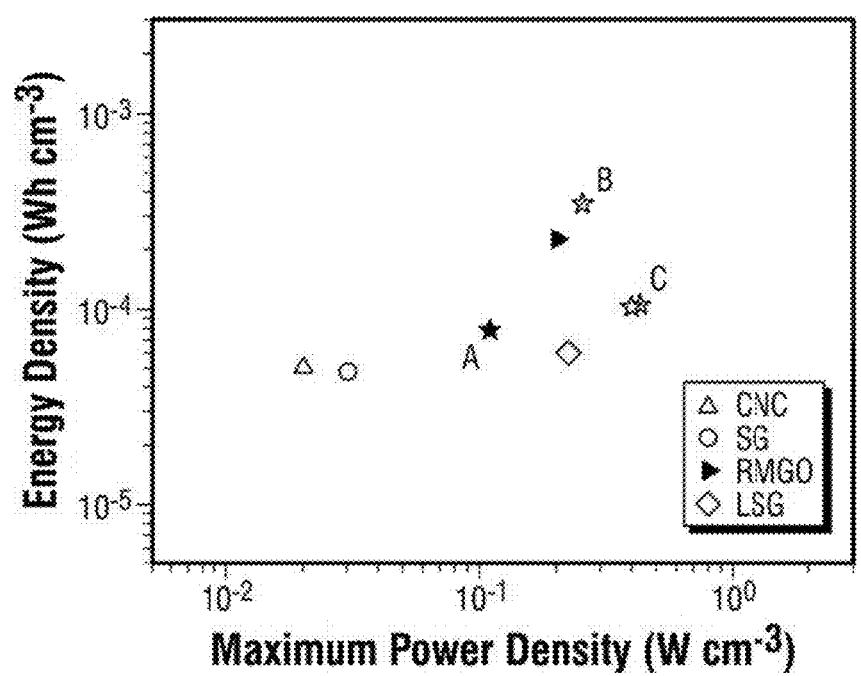
FIG. 11 is a plot of energy density (Wh cm$^{-3}$) vs. maximum power density (W cm$^{-3}$) and compares carbon based flexible supercapacitors using the same electrolyte.

Three flexible electrical devices were compared with other (non CNT) carbon based flexible supercapacitors (CNC: Carbon-nanocups, SG: single-layer graphene, RMGO: Reduced multi-layer graphene oxide, and LSG: Laser-scribed graphene) using the PVA/H$_3$PO$_4$ electrolyte. The results for the three coaxial CNT electrodes are shown with the labels A, B, and C in FIG. 11, which is a Ragone plot that summarizes the two main performance metrics, power and energy. Here the energy and power are normalized by the device volume, including the volume of the electrolyte. As shown in FIG. 11, the device performance of the coaxial CNT electrodes is comparable, if not superior, to devices assembled from the higher capacitance electrode materials. The flexible electrical devices provided higher device energy densities, even though the other electrode materials have a higher specific capacitance than CNTs. This is a result of the efficient space utilization enabled by the several factors of the device design as mentioned above, for example, from the use of the polymer electrolyte in the device fabrication and the inability of this polymer electrolyte to fully penetrate into the entirety of the porous electrode due to the high viscosity of polymer solutions. Regions inside the electrode where the polymer electrolyte does not reach will not be able to participate in the charge storage process and thus are deemed "inactive." Thus, electrodes with higher permeability will allow easier penetration of viscous polymer electrolytes.

A comparison of a flexible electrical device with known LSG electrodes, as an example, highlights two factors which enable the flexible electrical devices to outperform devices constructed from the higher capacitive graphene electrodes used for LSG electrodes. The calculations were simplified to two-dimensions by assuming equal lengths and carrying out the analysis on the cross-sectional area of the electrodes. The LSG electrodes were 7.6 microns thick and thus for equal comparison purposes the CNT yarn also had a diameter of 7.6 microns (i.e. electrodes of equal thickness). In the thickness-dependent areal capacitance tests an optimal thickness for SWNT electrodes was 2 microns when using the PVA/H$_3$PO$_4$ polymer electrolyte. Therefore, 2 microns was used as the penetration depth (δ) of electrolyte into the electrode for the example depicted in FIG. 12.

Figure 12:
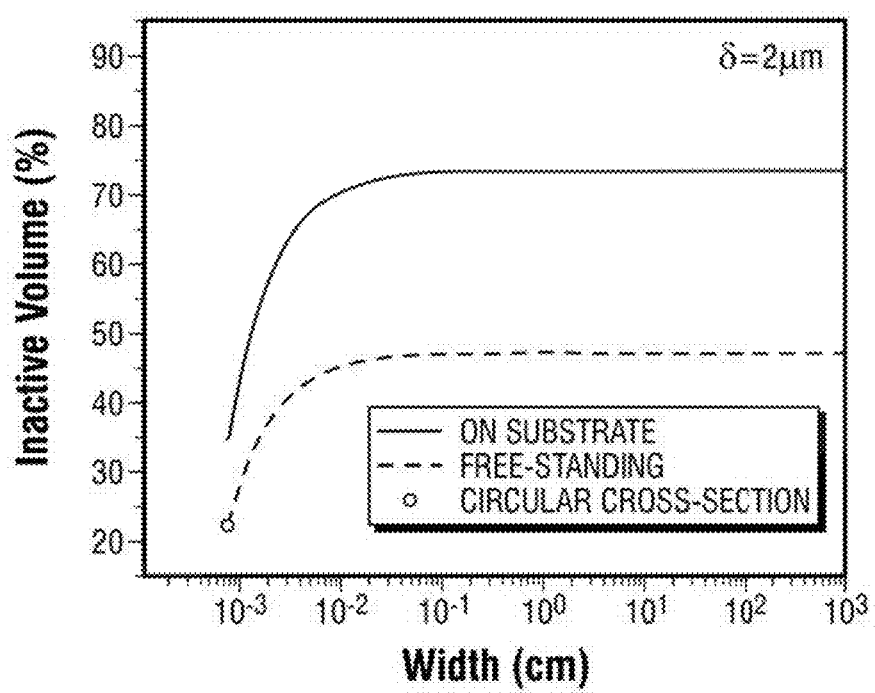
FIG. 12 is a graph of inactive volume (%) vs. width (cm) for rectangular cross-section electrodes with 7.6 micron thickness and an electrolyte penetration depth of 2 microns, in accordance with embodiments of the present disclosure.

FIG. 12 shows two cases for the width dependent percentage of inactive volume of an electrode with a rectangular cross-section. The first case assumed the electrolyte penetrated equally from all directions around the cross-section. This was true for the CNT yarn, as it was a free-standing material. The LSG electrodes, however, were supported by either flexible polymer substrates or Al foils and therefore the electrolyte penetration cannot occur from all directions. The second case was therefore calculated assuming penetration occurred from only the three exposed surfaces of the electrode. The graph also shows the percentage of inactive volume for the circular cross-section of the fiber electrode (since for the fiber diameter=thickness=width it was a single point on the X-axis at about 7.6 microns). As illustrated in FIG. 12, saturation occurred at relatively small widths (about 0.01 cm) and thus for some sample widths, the percentage of inactive volume for rectangular electrodes was about 47%. This was more than twice the amount of inactive volume of cylindrical electrodes of the same thickness (about 22%), even if electrolyte penetration from all sides is assumed. By restricting the electrolyte penetration to only the top face and two sides of the cross-section, the inactive volume increased to about 74%; which is more than three times the percentage of inactive volume present in a free-standing cylindrical electrode of the same thickness.

Figure 13:
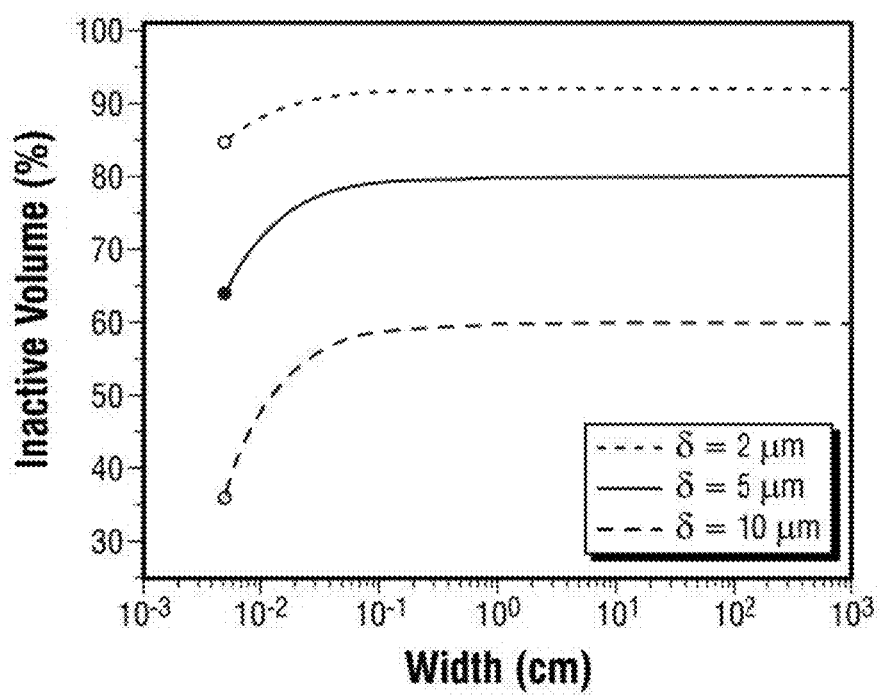
FIG. 13 is a graph of inactive volume (%) vs. width (cm) and depicts electrolyte penetration depth based on width of the inactive volume of 50 micron thick electrodes, in accordance with embodiments of the present disclosure. The result for the circular cross-section electrode is shown for each penetration depth as an open circle.

The extent of the penetration of polymer electrolytes into porous electrodes can be affected by several factors. These factors include the density and pore structure of the electrodes, the viscosity of the polymer electrolyte, and the fabrication methods and processing parameters used. To assess the effect of varying penetration depths, the same analysis was carried out using three different penetration depths on a thicker electrode. For these cases, the electrode thickness was assumed to be about 50 microns, which was the approximate typical diameter of the CNT yarn filaments. The width dependency for the inactive volume of rectangular cross-section electrodes at three different penetration depths (2, 5 and, 10 microns) is shown in FIG. 13. The results for the circular cross-section electrode (diameter=thickness=width=50 micron) is also shown for each penetration depth as the open circle. The results from FIG. 13 highlight the effect that the electrode design and fabrication process had on the final device properties. In some embodiments, full electrolyte coverage of the electrode was desirable. In other embodiments, free-standing cylindrical electrodes with high aspect ratios were the goal.

Example 6: Preparation of a Humidity Sensing Device

Figure 14:
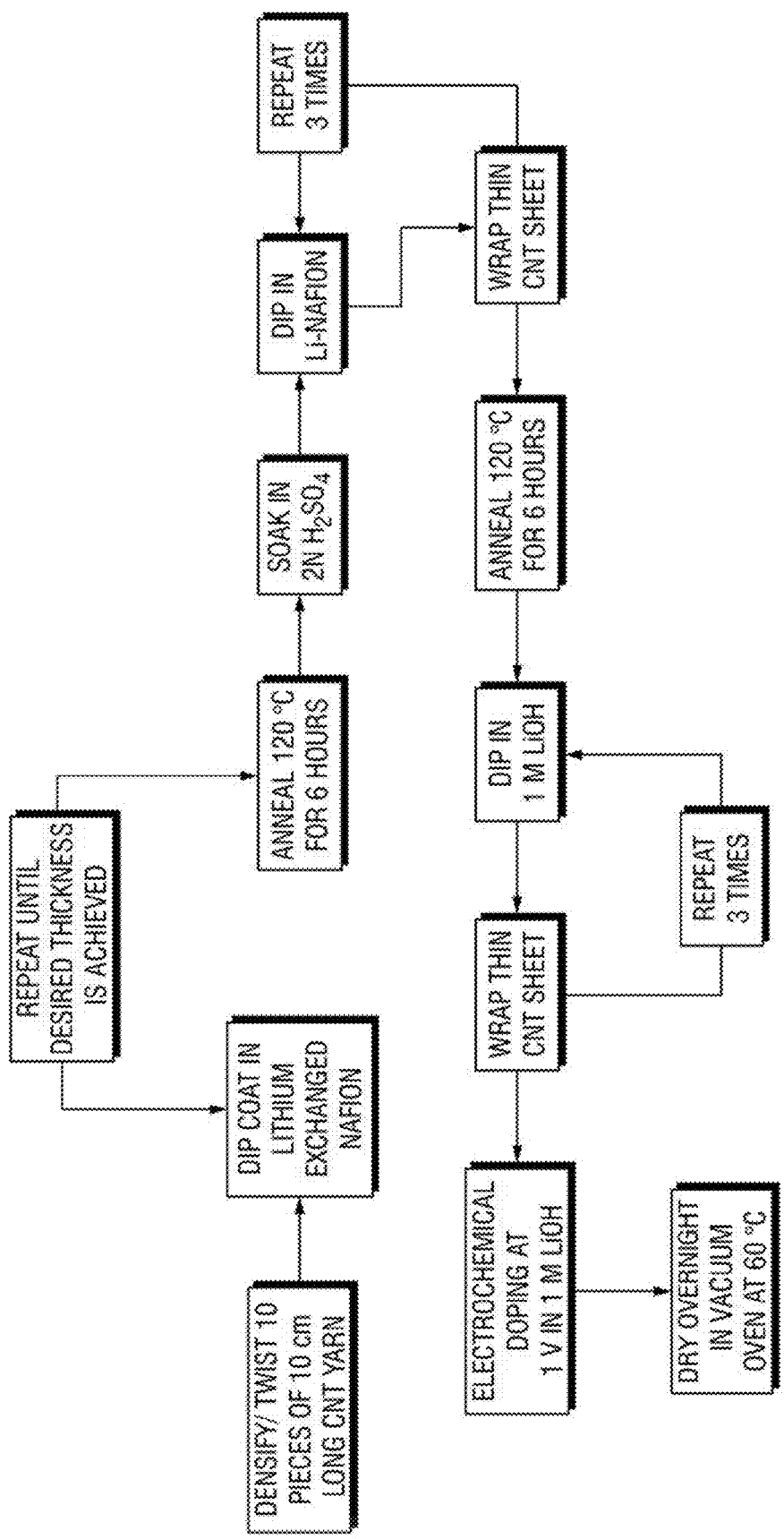
FIG. 14 is a process flow diagram that illustrates fabrication of a flexible electrical device in accordance with embodiments of the present disclosure.

Carbon nanotube yarn (CTex™) and non-woven sheets were purchased from Nanocomp Technologies, Inc., and were used as received. A Nafion® 117 solution and lithium hydroxide monohydrate (98%) were purchased from Sigma-Aldrich. The inner electrode was constructed by twisting multiple filaments of CNT yarn (length ~10 cm) together. The inner electrode was then coated with lithium exchanged Nafion (Li-Nafion) by several iterations of dip coating in Li-Nafion solution followed by annealing for 6 hours at 120° C. after each coating. The Li-Nafion was prepared by adding a 0.5 M LiOH drop-wise to the Nafion® 117 solution, while stirring, until the pH reached ~8. The outer electrode was applied by hand wrapping multiple layers of thin CNT sheets (~1 micron thickness) around the Li-Nafion coated region. This fabrication process is illustrated in FIG. 14.

Example 7: Measurement of Humidity

A controlled environment chamber from Electro-Tech Systems, Inc. was used to regulate the humidity via an ultrasonic humidifier and desiccant/pump dehumidification system and PID controller. The data from the chamber humidity sensor (capacitive film type) and the coaxial cell were simultaneously recorded using a custom LabView program (LabView 2009 SP1, Version 9.0.1f3). The OCP was measured using a nanovoltmeter from Keithley Instruments (Model 2182A) and connected to the computer (HP Presario CQ56 Notebook PC, 64-bit Windows 7) using a GPIB controller for hi-speed USB from National Instruments Corporation.

The controller compared the humidity set point (0-100 percent) to the data from a temperature-compensated humidity sensor within the chamber and regulated the power to the humidifier and dehumidifier systems in order to maintain the humidity at a desired level. A 4" diameter, 110 cfm fan circulated the air within the chamber to maintain a uniform atmosphere and to prevent condensation on the chamber humidity sensor. The specifications for the chamber stated the system was capable of maintaining the humidity to within 1% accuracy from 5% to 100% relative humidity (RH) at normal ambient conditions.

The data from the chamber humidity sensor and the sensing device made in Example 6 (solid-state yarn cell) were simultaneously recorded using a custom LabView program (LabView 2009 SP1, Version 9.0.1f3). The device OCP was measured using a nanovoltmeter from Keithley Instruments (Model 2182A) and connected to a computer (HP Presario CQ56 Notebook PC) using a GPIB controller for high-speed USB data transfers. The data acquisition rate of the LabView program was at least 1 point per second.

Figure 15:
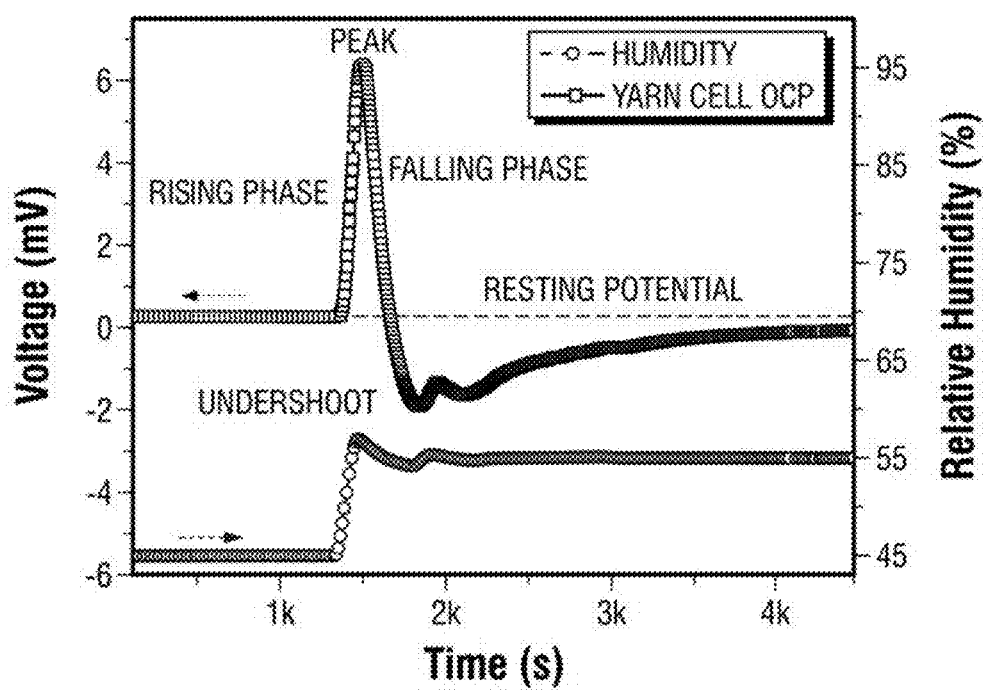
FIG. 15 is a graph of voltage (mV) vs. time (s) and relative humidity (%) vs. time (s) for the OCP of a flexible electrical device (a yarn cell) in accordance with embodiments of the present disclosure.

FIG. 15 is an example of the typical response of the device OCP to the increase in humidity of the surrounding environment (a decrease in humidity produced a reciprocal response). The labeling in FIG. 15 borrows from the biology terminology used to describe cell membrane action potentials in excitable animal cells. The comparison is meant solely to aid in the description of the waveforms and in no way meant to imply any similarities, or lack thereof, to any of the physical or chemical mechanisms that produce the waveforms. Changes in the humidity induced action potential-like response waveforms in the device OCP where, after reaching a peak potential, the waveform would decrease and undershoot the initial OCP before slowly returning towards the resting potential.

Figure 16A:
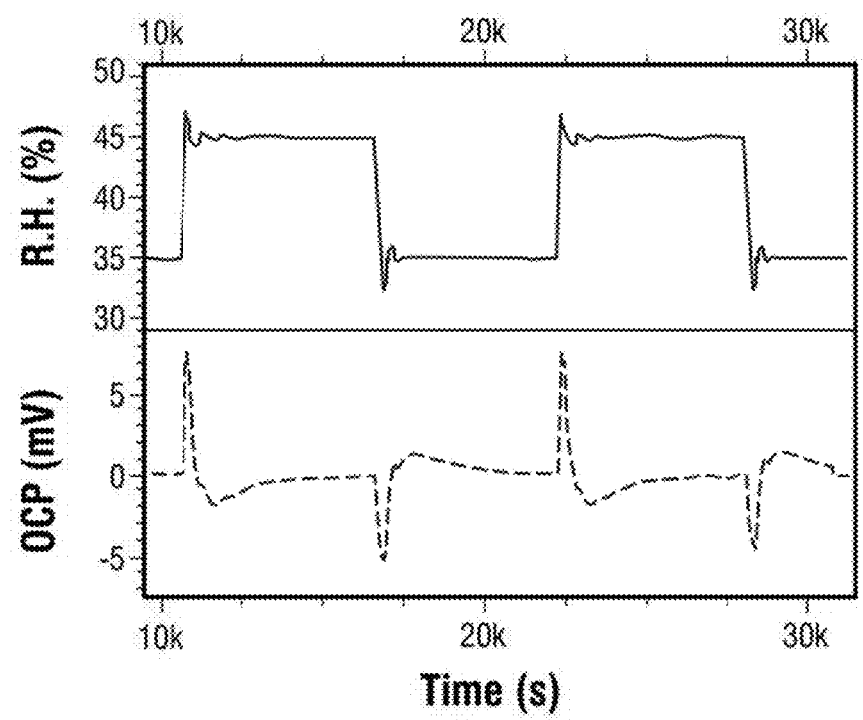
FIGS. 16A-16C are graphs of relative humidity (%) vs. time (s) and OCP (mV) vs. time (s) and comparing OCP response with a commercial humidity sensor response during cycling of the relative humidity between 35% and 45% (FIG. 16A), 45% and 55% (FIG. 16B) and 55% and 65% (FIG. 16C) in accordance with embodiments of the present disclosure.
Figure 16B:
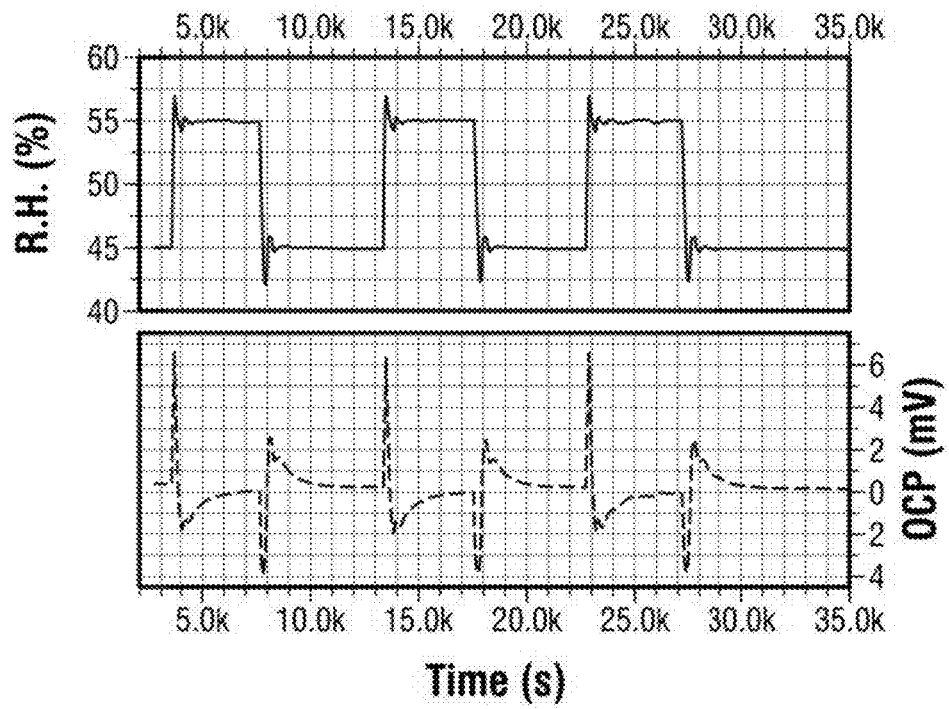
Figure 16C:
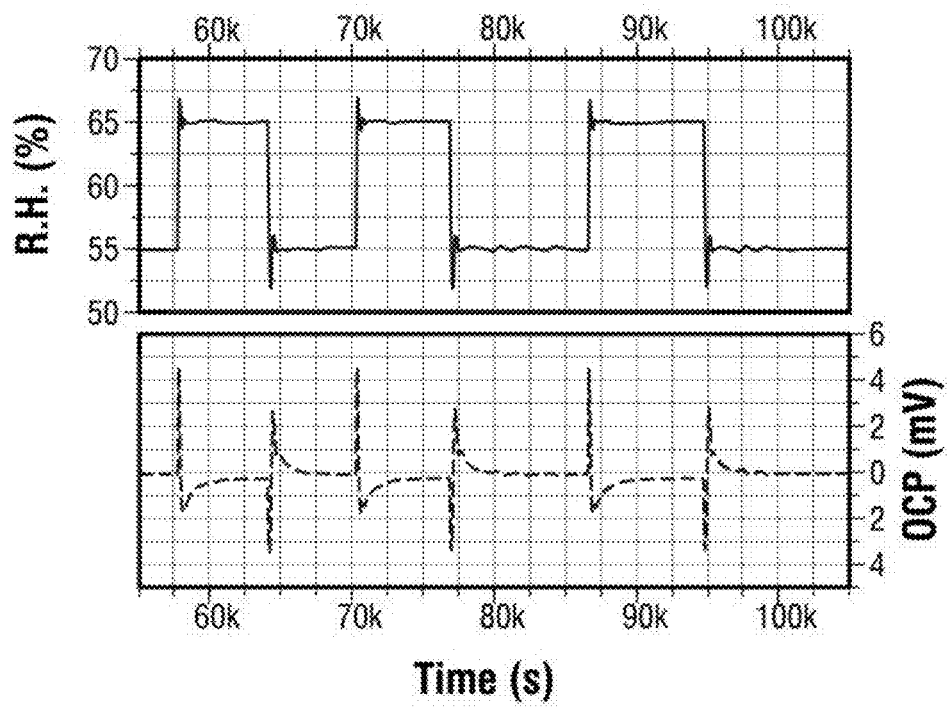
Figure 17A:
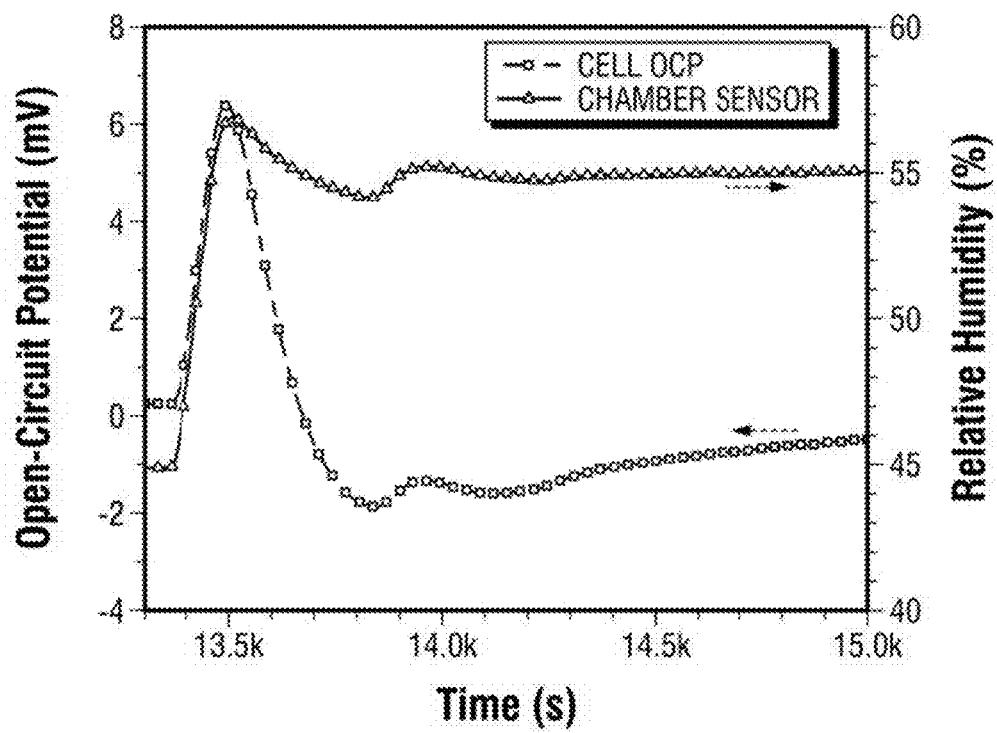
FIGS. 17A-17B are graphs of OCP (mV) vs. time (s) and relative humidity (%) vs. time (s) over different periods. The OCP showed small oscillations near the humidity set points following an increase and/or a decrease in relative humidity.
Figure 17B:
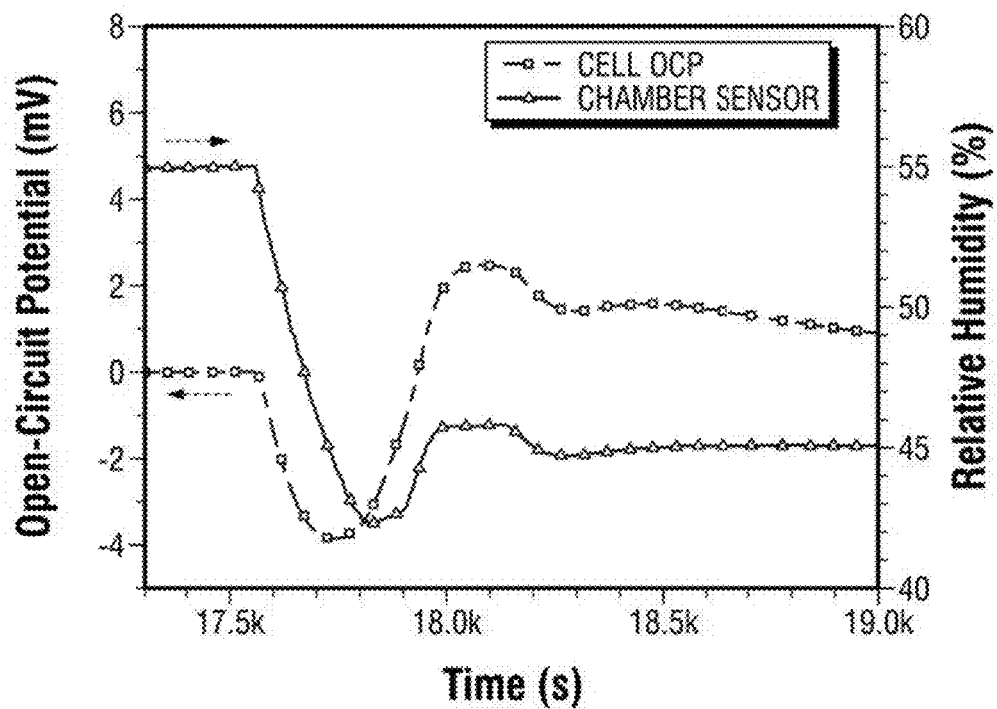

In FIGS. 16A-16C, the repeatability of the OCP response was investigated by performing three iterations of a 10% increase, 10% decrease cycling of the RH at three different humidity levels: 35%-45% (FIG. 16A), 45%-55% (FIG. 16B), and 55%-65% (FIG. 16C) are depicted. Following each step change, the humidity was kept constant for at least 1 hour to allow the OCP to return to a quasi-equilibrium/resting potential prior to each humidity step change. In FIGS. 17A-17B, data from a commercial humidity sensor was overlaid with the OCP of the device (coaxial electrode) for a 10% step-change in the RH from 45% to 55% (FIG. 17A) and for a 10% decrease from 55% to 45% (FIG. 17B).

Figure 18:
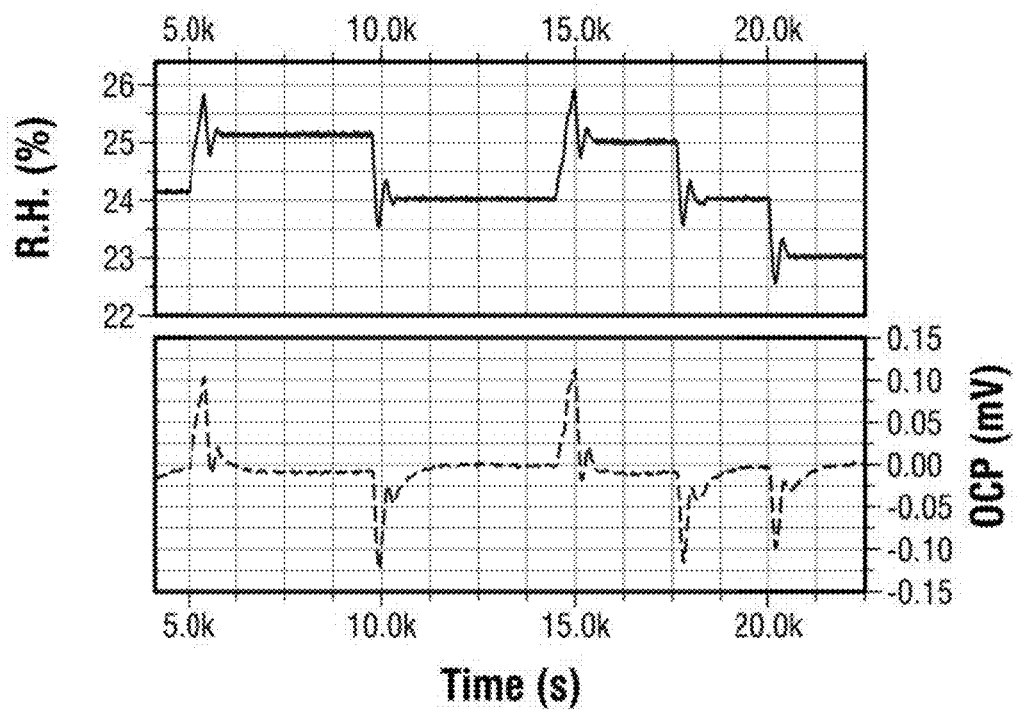
FIG. 18 shows graphs of relative humidity (%) vs. time (s) and OCP (mV) vs. time (s), measured over the same period. The OCP responded to changes from as little as a 1% change in the relative humidity.

To test the sensitivity of the coaxial electrode, the magnitude of the change in humidity was decreased from 10% to 1%. FIG. 18 shows the response from the coaxial electrode compared with the commercial sensor when the humidity was cycled between 24% and 25% relative humidity. An additional 1% decrease from 24% to 23% was included as the final event to show the dependency of the OCP peak amplitude on the initial and final humidity of the event.

Figure 19:
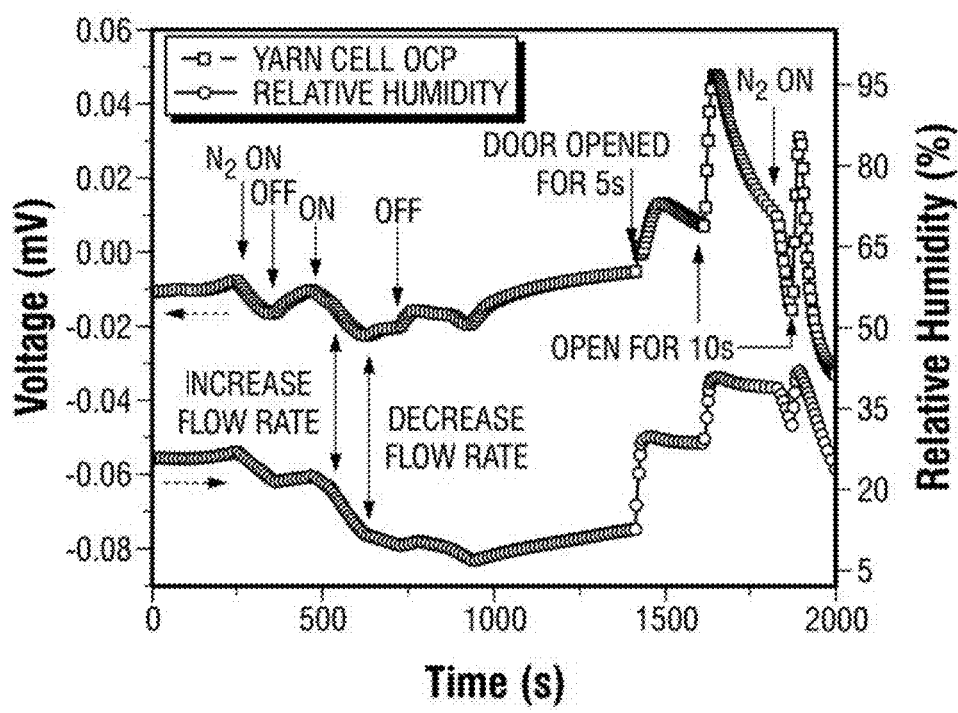
FIG. 19 is a graph of voltage (mV) vs. time (s) and relative humidity (%) vs. time (s). It shows the change in OCP for a sensing device (a yarn cell) according to an embodiment of the present disclosure operated in a UHP N$_2$ atmosphere (used to decrease humidity) controlled chamber. Changes in the chamber atmosphere were made and detected by the sensing device as shown.

To elucidate possible mechanisms of the OCP change, the response was also characterized using different methods to induce a change in humidity (other than the humidifier/dehumidifier associated with the environmental chamber). The chamber's method to increase the humidity required pumping in saturated air and created the possibility for associated increases to the chamber pressure. To test whether the underlying mechanism of the OCP change was due to this pressure change, the humidity was decreased by injecting ultra-high purity nitrogen gas with <1 ppm $H_2O$ (UHP300, Airgas) into the chamber. FIG. 19 shows the OCP response of the device (Yarn cell OCP) to the $N_2$ gas flow and the opening and closing of the chamber door. The gas flow was shut on/off and the door opened/closed at random intervals to demonstrate the responsiveness of the device when it is not given time to return to the resting potential. As depicted in FIG. 19, this method resulted in an increase in the pressure of the chamber but a decrease in the relative humidity. The humidity could then be increased by simply opening the chamber door and exposing to the laboratory atmosphere (lab humidity was typically around 45%~65% relative humidity).

Example 8: Measurement of Short-Circuit Current

A controlled environment chamber from Electro-Tech Systems, Inc. was used to regulate the humidity via an ultrasonic humidifier and desiccant/pump dehumidification system and PID controller. The data from the chamber humidity sensor (capacitive film type) and the coaxial cell were simultaneously recorded using a custom LabView program (LabView 2009 SP1, Version 9.0.1f3). A VersaSTAT3 with Frequency Response Analyzer upgrade from Princeton Applied Research was used in Zero Resistance Ammeter mode to measure the short-circuit current of the cell.

The controller compared the humidity set point (0-100 percent) to the data from a temperature-compensated humidity sensor within the chamber and regulated the power to the humidifier and dehumidifier systems in order to maintain the humidity at a desired level. A 4" diameter, 110 cfm fan circulated the air within the chamber to maintain a uniform atmosphere and to prevent condensation on the chamber humidity sensor. The specifications for the chamber stated the system was capable of maintaining the humidity to within 1% accuracy from 5% to 100% relative humidity (RH) at normal ambient conditions.

The data from the chamber humidity sensor and the sensing device made in Example 6 (solid-state yarn cell) were simultaneously recorded using a custom LabView program (LabView 2009 SP1, Version 9.0.1f3). The data acquisition rate of the LabView program was at least 1 point per second.

Figure 23:
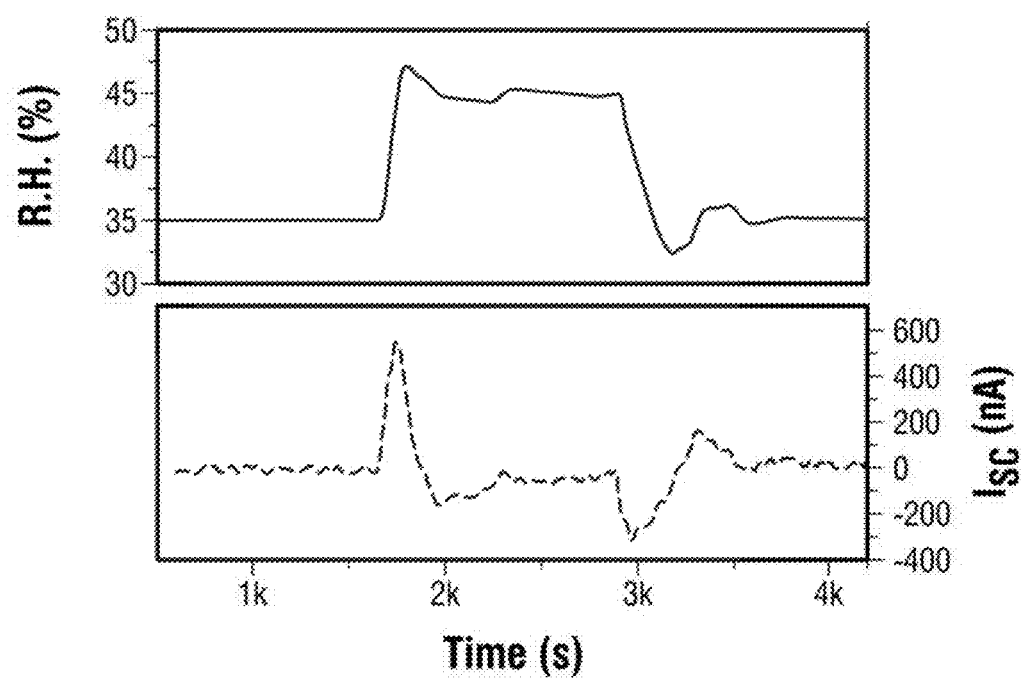
FIG. 23 is a graph of relative humidity (%) vs. short-circuit current $I_{sc}$ (nA) during cycling of the relative humidity between 35% and 45% in accordance with embodiments of the present disclosure.

The measurement of the short-circuit current of the cell in response to a 10% increase in the relative humidity from 35% to 45% and a 10% decrease from 45% back to 35% is shown in FIG. 23 to demonstrate the potential power output of the device. With a device volume of ~0.035 cm$^3$, the peak short-circuit current reached in FIG. 23 of ~600 nA is over 17 µA cm$^{-3}$ of volumetric current density.

Modifications and variations of the methods and devices described herein will be obvious to those skilled in the art from the foregoing detailed description. Such modifications and variations are intended to come within the scope of the appended claims.

We claim:

1. A method for fabricating an electrical component, the method comprising:
   providing an inner electrode which comprises one or more carbon nanotube fibers;
   coating the inner electrode with a polymer electrolyte to form a polymer-coated inner electrode having an exterior surface; and
   attaching an outer electrode, which comprises carbon nanotube sheets, to at least a first portion of the exterior surface of the polymer-coated inner electrode,
   thereby forming a flexible electrical component having a fiber geometry.

2. The method of claim 1, wherein before the coating, the inner electrode is at least partially submerged in an electrolyte solution while an electrical charge is applied across the inner electrode.

3. The method of claim 1, wherein the exterior surface of the polymer-coated inner electrode comprises a cylindrical surface.

4. The method of claim 3, wherein the attaching comprises attaching the outer electrode around the cylindrical surface to form an overlap region.

5. The method of claim 4, wherein the overlap region is in an elongated cylindrical shape, such that the flexible electrical device is a coaxial electrode.

6. The method of claim 1, wherein the inner carbon nanotube electrode comprises one or more filaments of a carbon nanotube yarn.

7. The method of claim 3, wherein the outer electrode is not attached to at least a second portion of the cylindrical surface, and the cylindrical surface has first and second electrode ends.

8. The method of claim 7, further comprising applying a silver paste, silver paint, or other conductive material to the first and second electrode ends.

9. The method of claim 1, wherein the polymer electrolyte is a gel and the flexible electrical component is a flexible electrical energy storage or harvesting device.

10. The method of claim 1, further comprising:
    connecting a first measurement contact to a surface of the inner electrode; and
    connecting a second measurement contact to a surface of the outer electrode,
    wherein the flexible electrical component is configured as a flexible sensing device.

11. The method of claim 10, wherein the polymer electrolyte comprises a sulfonated tetrafluoroethylene based fluoropolymer-copolymer electrolyte.

12. The method of claim 10, wherein the first and second measurement contacts are operably connected to a potentiostat.

* * * * *